US009326665B2

(12) United States Patent
Slenker et al.

(10) Patent No.: US 9,326,665 B2
(45) Date of Patent: May 3, 2016

(54) SURGICAL INSTRUMENT, SYSTEM, AND METHOD FOR BIOFILM REMOVAL

(75) Inventors: Dale E. Slenker, Jacksonville, FL (US); John R. Prisco, Jacksonville, FL (US); Cecil O. Lewis, Jacksonville, FL (US); Gerould W. Norman, Jacksonville, FL (US); Robert K. Vaccaro, Ponte Vedra Beach, FL (US); Isaac C. Perry, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 2486 days.

(21) Appl. No.: 11/697,789

(22) Filed: Apr. 9, 2007

(65) Prior Publication Data

US 2008/0249483 A1    Oct. 9, 2008

(51) Int. Cl.
*A61M 1/00* (2006.01)
*A61B 1/00* (2006.01)
(Continued)

(52) U.S. Cl.
CPC .............. *A61B 1/0055* (2013.01); *A61B 1/015* (2013.01); *A61B 1/2275* (2013.01); *A61B 1/233* (2013.01); *A61M 1/0058* (2013.01); *A61M 3/0258* (2013.01); *A61M 3/0279* (2013.01); *A61M 25/0147* (2013.01); *A61B 17/24* (2013.01); *A61B 2017/00314* (2013.01); *A61B 2017/242* (2013.01); *A61B 2217/007* (2013.01)

(58) Field of Classification Search
CPC ...... A61B 1/00091; A61B 1/015; A61B 1/12; A61B 2217/007; A61B 2217/005; A61B 17/3203; A61B 2017/320084; A61B 17/1688; A61B 17/32037; A61M 1/0064; A61M 1/0039; A61M 1/0058; A61M 1/0084; A61M 3/0283; A61M 25/0147
See application file for complete search history.

(56) References Cited

U.S. PATENT DOCUMENTS 1,487,252 A    3/1924   Lore
1,843,169 A    2/1932   McKesson
(Continued)

FOREIGN PATENT DOCUMENTS

KR    0289606 Y1    9/2002
KR    0439992 B1    7/2004
(Continued)

OTHER PUBLICATIONS

Y. Zhang et al., "Detection of *Streptococcus pneumoniae* in Whole Blood by PCR," Journal of Clinical Microbiology, Mar. 1995, pp. 596-601.
(Continued)

*Primary Examiner* — Nathan R Price
*Assistant Examiner* — William Carpenter
(74) *Attorney, Agent, or Firm* — Dicke, Billig & Czaja, PLLC

(57) ABSTRACT

Systems and methods for removal of bacterial biofilm from a target site of a human patient includes a surgical instrument having an introducer for bodily insertion and maintaining an irrigation duct and a nozzle. A distal portion of the introducer is transitionable between a plurality of bend angles relative to a proximal portion thereof. In particular, the instrument is adapted to independently maintain the distal portion at each of the plurality of bend angles relative to the proximal portion. The nozzle is maintained relative to the distal portion of the introducer and is adapted to dispense pressurized irrigant from the irrigation duct toward a layer of bacterial biofilm.

23 Claims, 20 Drawing Sheets

(51) Int. Cl.
*A61M 31/00* (2006.01)
*A61B 1/005* (2006.01)
*A61M 25/01* (2006.01)
*A61B 1/015* (2006.01)
*A61B 1/227* (2006.01)
*A61B 1/233* (2006.01)
*A61M 3/02* (2006.01)
*A61B 17/24* (2006.01)
*A61B 17/00* (2006.01)

(56) References Cited

U.S. PATENT DOCUMENTS

| | | | |
|---|---|---|---|
| 1,987,907 A | 1/1935 | Jenkins | |
| 2,243,299 A | 5/1941 | Travers | |
| 2,280,992 A | 4/1942 | Wright et al. | |
| 2,812,765 A | 11/1957 | Tofflemire | |
| 3,208,145 A | 9/1965 | Turner | |
| 3,452,745 A * | 7/1969 | Spitz | A61C 17/028 601/161 |
| 3,470,876 A | 10/1969 | Barchilon | |
| 3,749,090 A | 7/1973 | Stewart | |
| 3,799,151 A * | 3/1974 | Fukaumi | A61B 1/0055 600/142 |
| 3,980,078 A | 9/1976 | Tominaga | |
| 4,282,867 A | 8/1981 | Du Toit | |
| 4,299,221 A | 11/1981 | Phillips et al. | |
| 4,397,640 A | 8/1983 | Haug et al. | |
| 4,408,598 A | 10/1983 | Ueda | |
| 4,436,087 A * | 3/1984 | Ouchi | A61B 1/0008 600/106 |
| 4,487,600 A | 12/1984 | Brownlie et al. | |
| 4,517,962 A | 5/1985 | Heckele | |
| 4,519,385 A | 5/1985 | Atkinson et al. | |
| 4,526,573 A | 7/1985 | Lester et al. | |
| 4,573,979 A | 3/1986 | Blake | |
| 4,583,531 A | 4/1986 | Mattchen | |
| 4,604,089 A | 8/1986 | Santangelo et al. | |
| 4,617,013 A | 10/1986 | Betz | |
| 4,680,026 A | 7/1987 | Weightman et al. | |
| 4,696,669 A | 9/1987 | Menhusen | |
| 4,708,717 A | 11/1987 | Deane et al. | |
| 4,776,840 A | 10/1988 | Freitas et al. | |
| 4,801,292 A | 1/1989 | Watson | |
| 4,881,523 A | 11/1989 | Heckele | |
| 4,911,148 A | 3/1990 | Sosnowski et al. | |
| 4,941,872 A | 7/1990 | Felix et al. | |
| 4,964,849 A | 10/1990 | Robicsek | |
| 4,979,497 A | 12/1990 | Matsura et al. | |
| 4,991,565 A | 2/1991 | Takahashi et al. | |
| 4,991,957 A * | 2/1991 | Sakamoto | A61B 1/0005 356/241.4 |
| 5,100,377 A | 3/1992 | Freitas et al. | |
| 5,147,292 A | 9/1992 | Kullas et al. | |
| 5,170,774 A | 12/1992 | Heckele | |
| 5,199,950 A | 4/1993 | Schmitt et al. | |
| 5,201,908 A | 4/1993 | Jones | |
| 5,203,769 A | 4/1993 | Clement et al. | |
| 5,224,929 A | 7/1993 | Remiszewski | |
| 5,230,704 A | 7/1993 | Moberg et al. | |
| 5,231,989 A | 8/1993 | Middleman et al. | |
| 5,257,618 A * | 11/1993 | Kondo | G02B 23/26 138/120 |
| 5,286,253 A | 2/1994 | Fucci | |
| 5,295,956 A | 3/1994 | Bales et al. | |
| 5,312,327 A | 5/1994 | Bales et al. | |
| 5,314,406 A | 5/1994 | Arias et al. | |
| 5,318,526 A | 6/1994 | Cohen | |
| 5,322,503 A | 6/1994 | Desai | |
| 5,325,845 A * | 7/1994 | Adair | A61B 1/0055 600/114 |
| 5,328,467 A | 7/1994 | Edwards et al. | |
| 5,342,299 A | 8/1994 | Snoke et al. | |
| 5,354,267 A | 10/1994 | Niermann et al. | |
| 5,372,587 A | 12/1994 | Hammerslag et al. | |
| 5,378,234 A | 1/1995 | Hammerslag et al. | |
| 5,383,852 A | 1/1995 | Stevens-Wright | |
| 5,386,817 A | 2/1995 | Jones | |
| 5,397,321 A | 3/1995 | Houser et al. | |
| 5,429,596 A | 7/1995 | Arias et al. | |
| 5,437,636 A | 8/1995 | Snoke et al. | |
| 5,438,975 A * | 8/1995 | Miyagi | A61B 1/00071 600/109 |
| 5,443,445 A | 8/1995 | Peters et al. | |
| 5,462,527 A | 10/1995 | Stevens-Wright et al. | |
| 5,484,402 A | 1/1996 | Saravia et al. | |
| 5,496,267 A * | 3/1996 | Drasler | A61B 17/32037 604/22 |
| 5,496,314 A | 3/1996 | Eggers | |
| 5,520,222 A | 5/1996 | Chikama | |
| 5,554,112 A | 9/1996 | Walbrink et al. | |
| 5,575,752 A | 11/1996 | Yabe et al. | |
| 5,575,756 A | 11/1996 | Karasawa et al. | |
| 5,607,391 A | 3/1997 | Klinger et al. | |
| 5,609,573 A | 3/1997 | Sandock | |
| 5,709,698 A | 1/1998 | Adams et al. | |
| 5,792,098 A | 8/1998 | Felix et al. | |
| 5,842,973 A | 12/1998 | Bullard | |
| 5,846,183 A * | 12/1998 | Chilcoat | A61B 1/00142 600/112 |
| 5,855,549 A | 1/1999 | Newman | |
| 5,928,191 A | 7/1999 | Houser et al. | |
| 5,944,689 A | 8/1999 | Houser et al. | |
| 5,989,183 A | 11/1999 | Reisdorf et al. | |
| 5,993,410 A | 11/1999 | Vincent et al. | |
| 6,030,360 A | 2/2000 | Biggs | |
| 6,086,542 A | 7/2000 | Glowa et al. | |
| 6,110,103 A | 8/2000 | Donofrio | |
| 6,126,633 A | 10/2000 | Kaji et al. | |
| 6,174,280 B1 | 1/2001 | Oneda et al. | |
| 6,179,776 B1 | 1/2001 | Adams et al. | |
| 6,282,442 B1 | 8/2001 | DeStefano et al. | |
| 6,293,957 B1 * | 9/2001 | Peters | A61B 17/32002 606/167 |
| 6,364,853 B1 | 4/2002 | French et al. | |
| 6,375,635 B1 * | 4/2002 | Moutafis | A61B 17/3203 604/22 |
| 6,508,810 B1 * | 1/2003 | Ouchi | A61B 1/00091 239/491 |
| 6,551,302 B1 | 4/2003 | Rosinko et al. | |
| 6,599,237 B1 | 7/2003 | Singh | |
| 6,623,445 B1 | 9/2003 | Nelson et al. | |
| 6,652,488 B1 | 11/2003 | Cover et al. | |
| 6,679,834 B2 | 1/2004 | Stahl et al. | |
| 6,712,757 B2 * | 3/2004 | Becker | A61B 1/00091 600/114 |
| 6,712,759 B2 | 3/2004 | Muller | |
| 6,746,419 B1 | 6/2004 | Arnett et al. | |
| 6,770,050 B2 | 8/2004 | Epstein | |
| 6,811,544 B2 | 11/2004 | Schaer | |
| 6,863,668 B2 | 3/2005 | Gillespie et al. | |
| 6,907,879 B2 | 6/2005 | Drinan et al. | |
| 6,918,902 B2 | 7/2005 | French et al. | |
| 6,939,293 B2 | 9/2005 | Conteas | |
| 6,945,956 B2 | 9/2005 | Waldhauser et al. | |
| 7,025,759 B2 | 4/2006 | Muller | |
| 7,144,383 B2 | 12/2006 | Arnett et al. | |
| 8,206,349 B2 * | 6/2012 | Slenker | A61B 1/00091 604/109 |
| 2001/0025134 A1 | 9/2001 | Bon et al. | |
| 2003/0176767 A1* | 9/2003 | Long | A61B 1/0014 600/106 |
| 2003/0176769 A1 | 9/2003 | Soble et al. | |
| 2003/0181934 A1 | 9/2003 | Johnston et al. | |
| 2004/0059191 A1 | 3/2004 | Krupa et al. | |
| 2004/0267213 A1 | 12/2004 | Knapp | |
| 2005/0075621 A1 | 4/2005 | Rontal | |
| 2005/0080396 A1* | 4/2005 | Rontal | A61B 17/22004 604/500 |
| 2005/0107853 A1 | 5/2005 | Krespi et al. | |
| 2005/0182353 A1 | 8/2005 | Schmidberger et al. | |
| 2005/0240147 A1 | 10/2005 | Makower et al. | |
| 2006/0004286 A1 | 1/2006 | Chang et al. | |
| 2006/0004323 A1 | 1/2006 | Chang et al. | |

(56) References Cited

U.S. PATENT DOCUMENTS

| | | | |
|---|---|---|---|
| 2006/0009678 A1 | 1/2006 | Jaffe et al. | |
| 2006/0015009 A1 | 1/2006 | Jaffe et al. | |
| 2006/0015010 A1 | 1/2006 | Jaffe et al. | |
| 2006/0025652 A1 | 2/2006 | Vargas | |
| 2006/0041186 A1 | 2/2006 | Vancaillie | |
| 2006/0063973 A1 | 3/2006 | Makower et al. | |
| 2006/0069343 A1 | 3/2006 | Rontal | |
| 2006/0084910 A1 | 4/2006 | Hoffman | |
| 2006/0095066 A1* | 5/2006 | Chang | A61F 11/002 606/199 |
| 2006/0100481 A1 | 5/2006 | Soble et al. | |
| 2006/0111615 A1 | 5/2006 | Danitz et al. | |
| 2006/0135961 A1* | 6/2006 | Rosenman | A61M 25/0045 606/108 |
| 2006/0210605 A1 | 9/2006 | Chang et al. | |
| 2006/0224103 A1 | 10/2006 | Rontal | |
| 2007/0264342 A1* | 11/2007 | Oliver | A61K 9/0043 424/486 |
| 2008/0214891 A1* | 9/2008 | Slenker et al. | 600/109 |
| 2008/0249483 A1* | 10/2008 | Slenker | A61B 1/0055 604/275 |

FOREIGN PATENT DOCUMENTS

| | | | | |
|---|---|---|---|---|
| WO | WO 2004006788 A1 * | 1/2004 | | A61B 17/32002 |
| WO | 2004006788 A1 | 7/2004 | | |

OTHER PUBLICATIONS

J. Christopher Post, MD et al., "Molecular Analysis of Bacterial Pathogens in Otitis Media with Effusion," JAMA, May 24-31, 1995, vol. 273, No. 20; 7 pgs.
E. M. Liederman, MD et al., "Analysis of Adult Otitis Media: Polymerase Chain Reaction Versus Culture for Bacteria and Viruses," Ann Otol Rhinol Laryngol 107:1998; pp. 10-16.
J. J. Aul, MD et al., "Comparative Evaluation and Culture and PCR for the Detection and Determination of Persistence of Bacterial Strains and DNAs in the Chinchilla Laniger Model of Otitis Media," Ann Otol Rhinol Laryngol 107:1998; pp. 508-513.
L. O. Bakaletz et al., "Blinded Multiplex PCR Analyses of Middle Ear and Nasopharyngeal Fluids from Chinchilla Models of Single- and Mixed-Pathogen-Induced Otitis Media," Clinical and Diagnostic Laboratory Immunology, Mar. 1998, pp. 219-224.
J.R. Dingman et al., "Correlation Between Presence of Viable Bacteria and Presence of Endotoxin in Middle-Ear Effusions," Journal of Clinical Microbiology, Nov. 1998, pp. 3417-3419.
J.W. Costerton, "Introduction to Biofilm," International Journal of Antimicrobial Agents 11 (1999); Dec. 2001; pp. 217-221.
J. Christopher Post, MD, PhD, "Direct Evidence of Bacterial Biofilms in Otitis Media," The Laryngoscope, Dec. 2001; pp. 2083-2094.
J.W. Costerson et al., "Battling Iofilms," Scientific American, Jul. 2001; pp. 75-81.
P.S. Mason et al., "Effect of Bacterial Endotoxin and Middle Ear Effusion on Ciliary Activity: Implications for Otitis Media," The Laryngoscope; Apr. 2002; pp. 676-680.
G.D. Ehrlich, PhD et al., "Mucosal Biofilm Formation on Middle-Ear Mucosa in the Chinchilla Model of Otitis Media," JAMA, Apr. 3, 2002, vol. 287, No. 13; pp. 1710-1715.
R.M. Donlan et al., "Biofilms: Survival Mechanisms of Clinically Relevant Microorganisms," Clinical Microbiology Reviews, Apr. 2002, pp. 167-193.
J. Cryer et al., "Evidence of Bactrial Biofilms in Human Chronic Sinusitis," Department of Otorhinolaryngology—Head and Neck Surgery, University of Pennsylvania Medical Center; 2004; pp. 155-158.
G.T. Rodeheaver, PhD, "Wound Cleansing, Wound Irrigation, Wound Disinfection," Chronic Wound Care: A Clinical Source Book for Healthcare Professionals, Third Edition, 2001; pp. 369-383.
J.N. Palmer MD, "Bacterial Biofilms: Do They Play a Role in Chronic Sinusitis?" Department of Otolaryngology—Head and Neck Surgery, Hospital of Pennsylvania, 2005; pp. 1193-1201.
A.Tripathi, MD et al., "*Staphylococcal* Exotoxins and Nasal Polyposis: Analysis of Systemic and Local Responses," American Journal of Rhinology, Jul.-Aug. 2005, vol. 19, No. 4; pp. 327-333.
J.E. Dohar, MD, MS et al., "Mucosal Biofilm Formation on Middle-Ear Mucosa in a Nonhuman Primate Model of Chronic Suppurative Otitis Media," The Laryngoscope, Aug. 2005; pp. 1469-1472.
B.J. Ferguson MD et al., "Demonstration of Biofilm in Human Bacterial Chronic Rhinosinusitis," American Journal of Rhinology, Sep.-Oct. 2005, vol. 19, No. 5, pp. 452-457.
L. Hall-Stoodley, PhD et al, "Direct Detection of Bacterial Biofilms on the Middle-Ear Mucosa of Children with Chronic Otitis Media," JAMA, Jul. 12, 2006, vol. 296, No. 2, pp. 202-211.
Z. Bendouah, BSC et al., "Biofilm Formation by *Staphylococcus aureus* and Pseudomonas Aeruginosa is Associated with an Unfavorable Evolution After Surgery for Chronic Sinusitis and Nasal Polyposis," American Academy of Otolaryngology—Head and Neck Surgery Foundation; 2006; pp. 991-996.
U.S. Appl. No. 11/621,453, filed Jan. 9, 2007.
U.S. Appl. No. 11/680,781, filed Mar. 1, 2007.
PCT Search Report (mailed Aug. 20, 2008); 11 pgs.

* cited by examiner

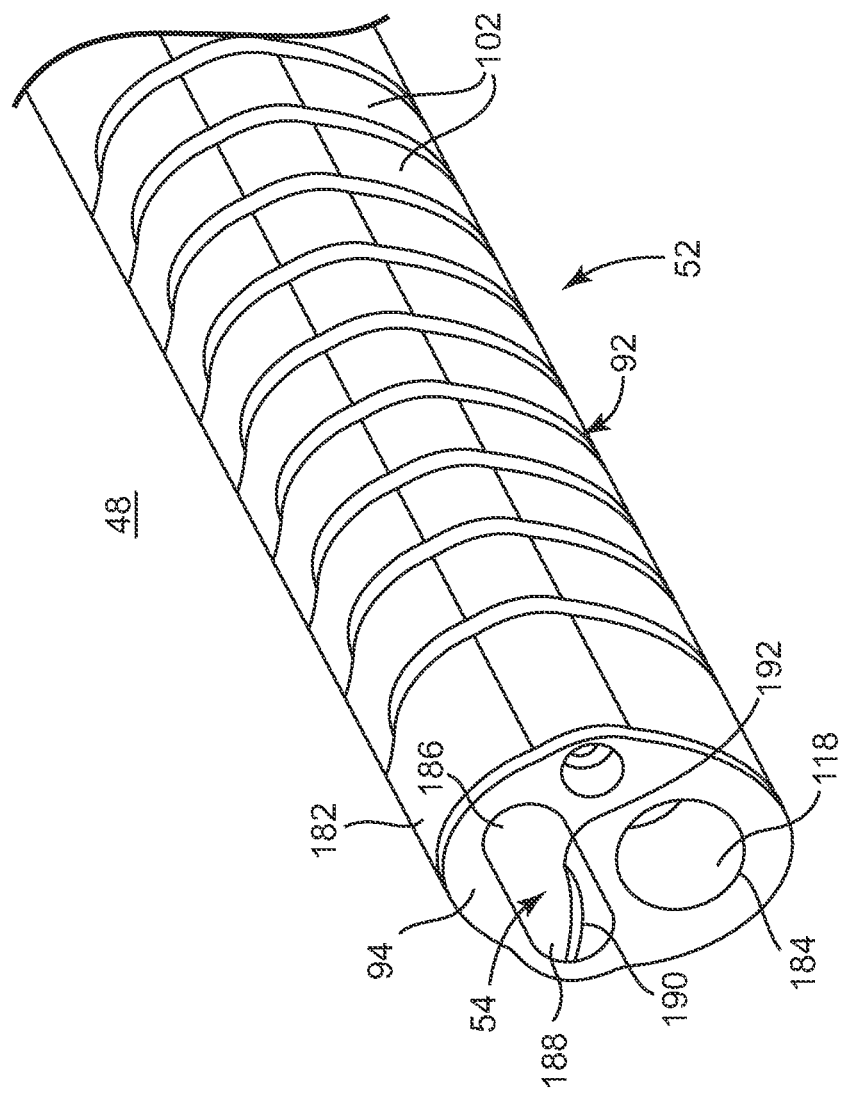

SURGICAL INSTRUMENT, SYSTEM, AND METHOD FOR BIOFILM REMOVAL

CROSS-REFERENCE TO RELATED APPLICATIONS

This application is related to U.S. application Ser. No. 11/621,453, filed Jan. 9, 2007, entitled "Surgical Systems and Methods for Biofilm Removal, Including a Sheath for Use Therewith," and to U.S. application Ser. No. 11/680,781, filed Mar. 1, 2007, entitled "Systems and Methods For Biofilm Removal, Including A Biofilm Removal Endoscope For Use Therewith," the entire teachings of both of which are incorporated herein by reference.

BACKGROUND OF THE INVENTION

Bacterial biofilms develop in a variety of bodily cavities, including those of the ear, such as the middle ear, and of the nose, such as the frontal or maxillary sinuses, for example. Once bacterial growth has been established, the bacteria will often aggregate, stop dividing, and begin forming protective bacterial biofilm layers, or "slime layers," comprised of polysaccharide matrices.

The protective bacterial biofilm interferes with the body's natural immune response as well as traditional methods of treatment. In particular, the bacteria emit exotoxins, which incite the body's immune system to respond with white cells. However, the bacterial biofilm interferes with the efficacy of the white cells' ability to attack the bacteria. The biofilm can also act as a barrier against topical administration of antibiotics and other medicaments. Biofilm-forming bacteria also present obstacles to traditional, antibiotic treatments that act to kill dividing bacteria. In particular, the bacteria in a biofilm-forming state may have already ceased cell division, rendering such antibiotics largely ineffective.

For example, relative to chronic rhinosinusitis and other similar ailments, bacteria in the nose can be viewed as a continuum. Some bacteria (e.g., certain strains of pseudomonas and staph aureus) form robust biofilms. Others (e.g., h. flu) form relatively mild biofilms. The biofilms may or may not include or contain fungi. Each of these microbes has a somewhat different or complimentary inflammatory pathway and interacts with the host's immune system differently. For example, staph aureus produces a lipopolysaccharide matrix that acts as an antigen and causes a host response, as well as toxins (e.g., staph exotin A and B, toxic shock syndrome toxin 1 and 2) that can produce an antigenic and even hyperantigenic superantigenic (hyperinflammatory) response. Recent literature suggests that chronic rhinosinusitis is an inflammatory response to bacterial biofilms. Other microbes can also produce inflammatory-inciting toxins. The sessile nature of the underlying bacteria and the tenaciousness of the biofilm make them difficult to treat.

Functional endoscopic sinus surgery (FESS) is a minimally invasive surgical procedure used to treat chronic rhinosinusitis, and possibly other infections of the sinuses. FESS opens up sinus air cells and sinus ostia (openings) with an instrument aided by an endoscope. The use of FESS as a sinus surgical method has now become widely accepted. The purpose of FESS is typically to restore normal drainage of the sinuses and to allow their ventilation. However, FESS does not address the bacterial biofilm concerns described above.

While ventilation surgery may incidentally cause some biofilms to slough off, many remain after surgery and it has been postulated that further therapies are required to remove bacterial biofilms in the paranasal sinuses and other bodily locations.

SUMMARY OF THE INVENTION

Some embodiments relate to a bacterial biofilm removal system including an instrument for removing bacterial biofilm from the target site. The instrument includes an introducer for bodily insertion. The introducer, in turn, includes a proximal portion and a distal portion. The distal portion is transitionable between a plurality of bend angles relative to the proximal portion. In particular, the instrument is adapted to independently maintain the distal portion at each of the plurality of bend angles relative to the proximal portion. The instrument also includes an irrigation duct for conveying irrigant and a nozzle in fluid communication with the irrigation duct. The nozzle is maintained relative to the distal portion of the introducer and is adapted to dispense pressurized fluid from the irrigation duct toward a layer of bacterial biofilm to scrub the bacterial biofilm from the target site. In some embodiments, the nozzle is rotatably maintained by the introducer. In other embodiments, the system further includes an optional endoscope system including an endoscope for imaging the target site.

Other embodiments relate to a method of removing bacterial biofilm from a target site of a human patient. A bacterial biofilm removal system is provided, the system including a surgical instrument. The instrument has an introducer maintaining an irrigation duct and a nozzle in fluid communication with the irrigation duct. The nozzle is positioned at a distal end of the introducer, with a distal portion of the introducer being articulatable relative to a proximal portion thereof. The distal portion of the introducer is surgically inserted into the patient. The nozzle is delivered proximate the target site, with the target site including a layer of bacterial biofilm adhered to a surface. A flow of pressurized irrigant is dispensed through the nozzle toward the target site to mechanically disrupt or remove a substantial portion of the layer of bacterial biofilm from the surface. In some embodiments, an endoscope is employed to assist in positioning the nozzle relative to the target site.

BRIEF DESCRIPTION OF THE DRAWINGS

FIG. 7 is an enlarged, perspective view of a distal portion of an introducer of the instrument of FIG. 2;

DETAILED DESCRIPTION OF THE INVENTION

Aspects of embodiments described herein relate to systems, methods, and apparatuses for one or more of reducing, removing, or preventing growth of bacterial biofilms. In particular, surgical biofilm removal systems, methods, and apparatuses adapted for such use will be understood with reference to the text and accompanying drawings.

Figure 1A:
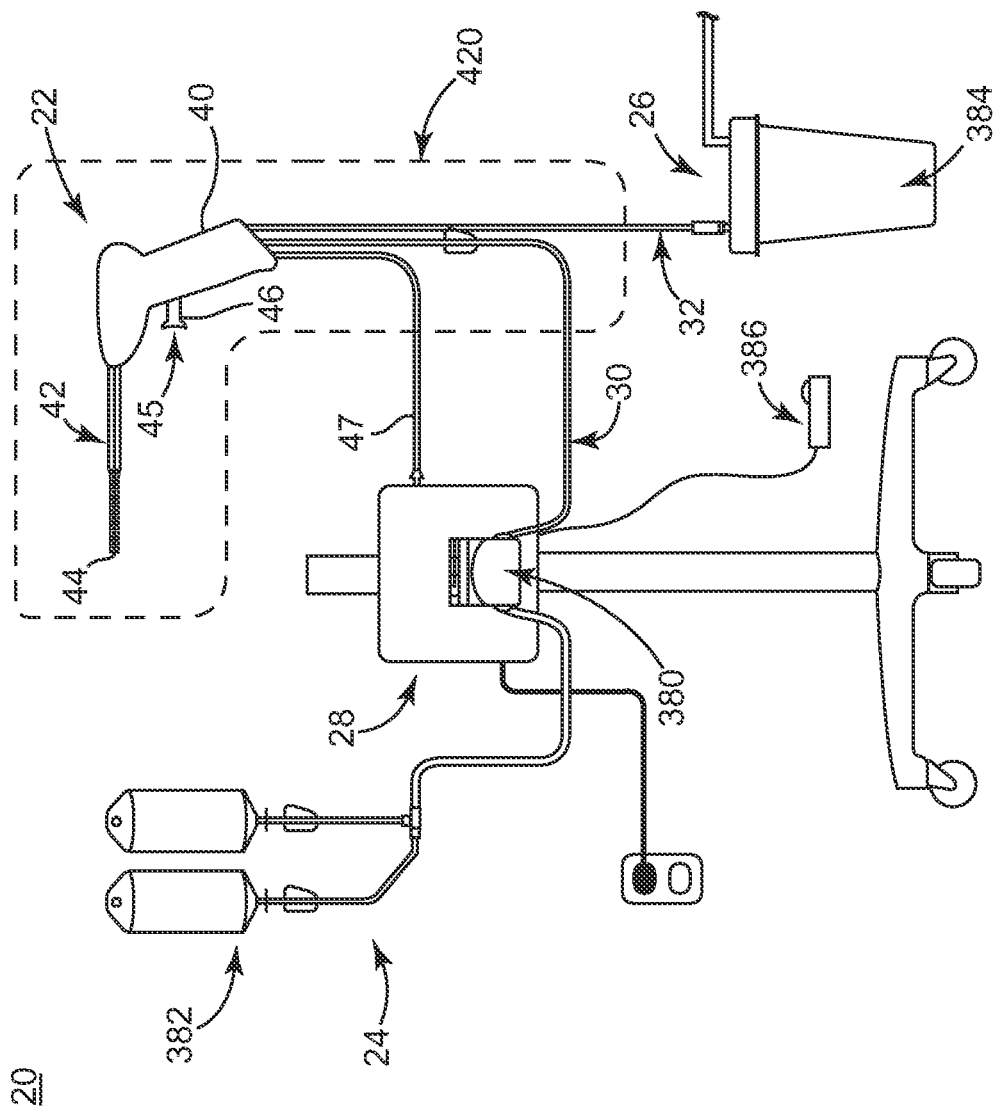
FIG. 1A is a schematic illustration of a surgical biofilm removal system in accordance with principles of the present disclosure.

FIG. 1A shows a surgical biofilm removal system 20 according to some embodiments. The system 20 includes a biofilm removal surgical instrument 22, a fluid source 24, a vacuum source 26 (referenced generally), and a controller 28. In general terms, the fluid source 24 provides fluid, or irrigant, to the instrument 22, for example via a fluid connector 30 (e.g., tubing). Conversely, the vacuum source 26 provides vacuum flow, or aspiratory flow, to the instrument 22, for example via a vacuum connector 32 (e.g., tubing). The controller 28 controls aspects of operation of the system 20 and is indicated as being generally associated with the instrument 22 and the fluid source 26.

Figure 1B:
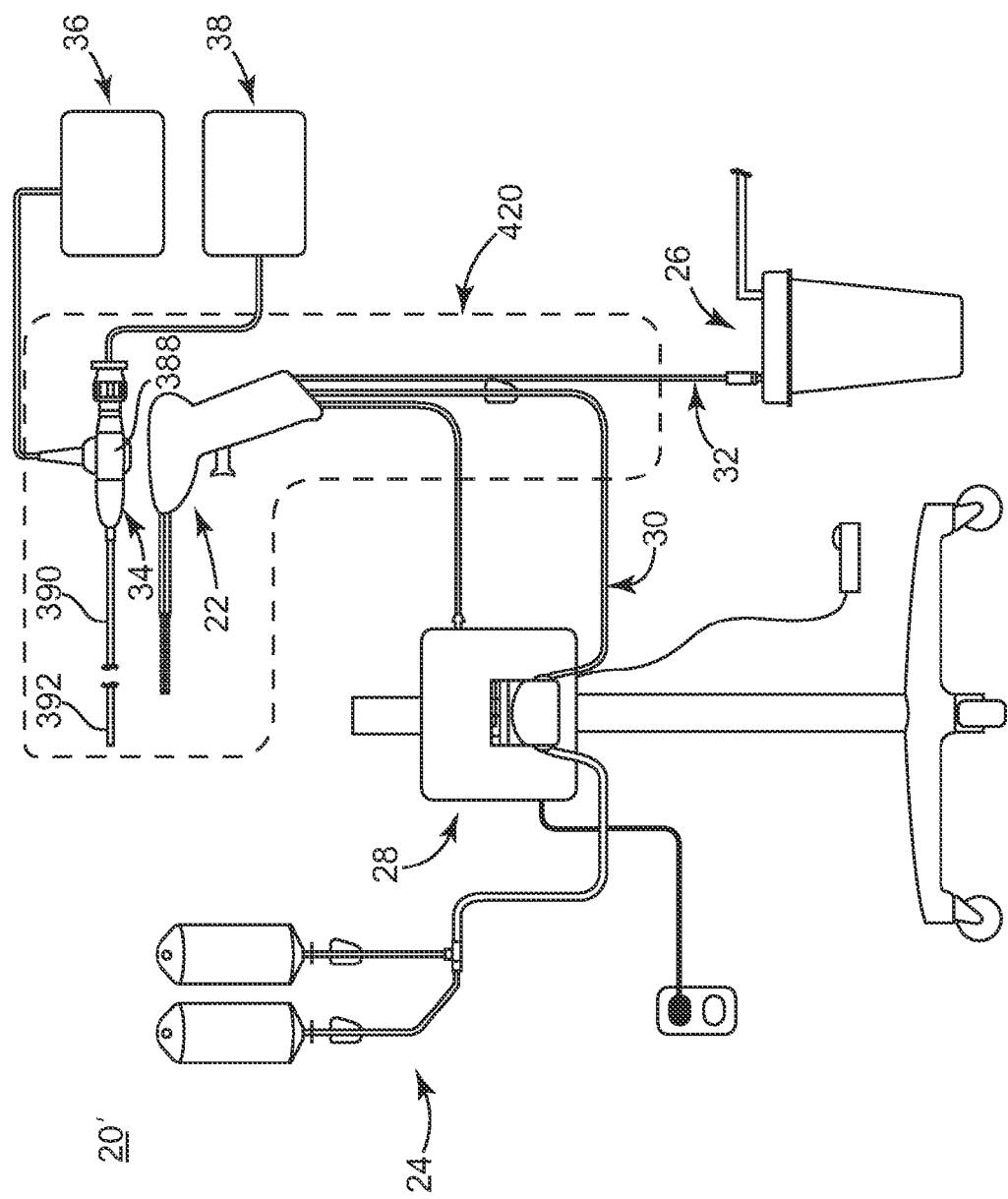
FIG. 1B is a schematic illustration of another surgical biofilm removal system in accordance with principles of the present disclosure.

The system 20 can include additional components. For example, another surgical biofilm removal system 20' is shown in FIG. 1B includes the same components as the system 20 (FIG. 1A), along with an optional endoscopic system including an endoscope 34 and related components such as a light source 36 and an imaging device 38. In general terms, the endoscope 34 can be of a conventional construction, with the light source 36 and the imaging device 38 facilitating visualization of a surgical area accessed by the biofilm removal surgical instrument 22 as described below. In other embodiments, however, the endoscope 34 and related components 36, 38 can be provided separately or apart from the system 20' and/or eliminated (such as with the system 20 of FIG. 1A).

The biofilm removal surgical instrument 22 can assume a variety of forms as described in greater detail below. In general terms, however, the instrument 22 includes a handle 40 and an introducer 42. The introducer 42 extends from the handle 40 and is sized for surgical insertion into a patient in a minimally invasive manner. The introducer 42 maintains a nozzle 44 (referenced generally) at a distal end thereof, as well as an irrigation duct (hidden in FIGS. 1A and 1B) that otherwise establishes a fluid connection between the nozzle 44 and the fluid connector 30. An aspiration duct (hidden in FIGS. 1A and 1B) can also be maintained by the introducer 42. Regardless, at least a portion of the introducer 42 is articulatable as described below for obtaining a desired spatial position of the nozzle 44, and for gaining access to specific sites within the body. Further, the handle 40 maintains a trigger assembly 45 that includes an actuator 46. Upon depression of the actuator 46, a signal is delivered to the controller 28 via a connector 47 to prompt delivery of irrigant to the instrument 22.

Figure 2:
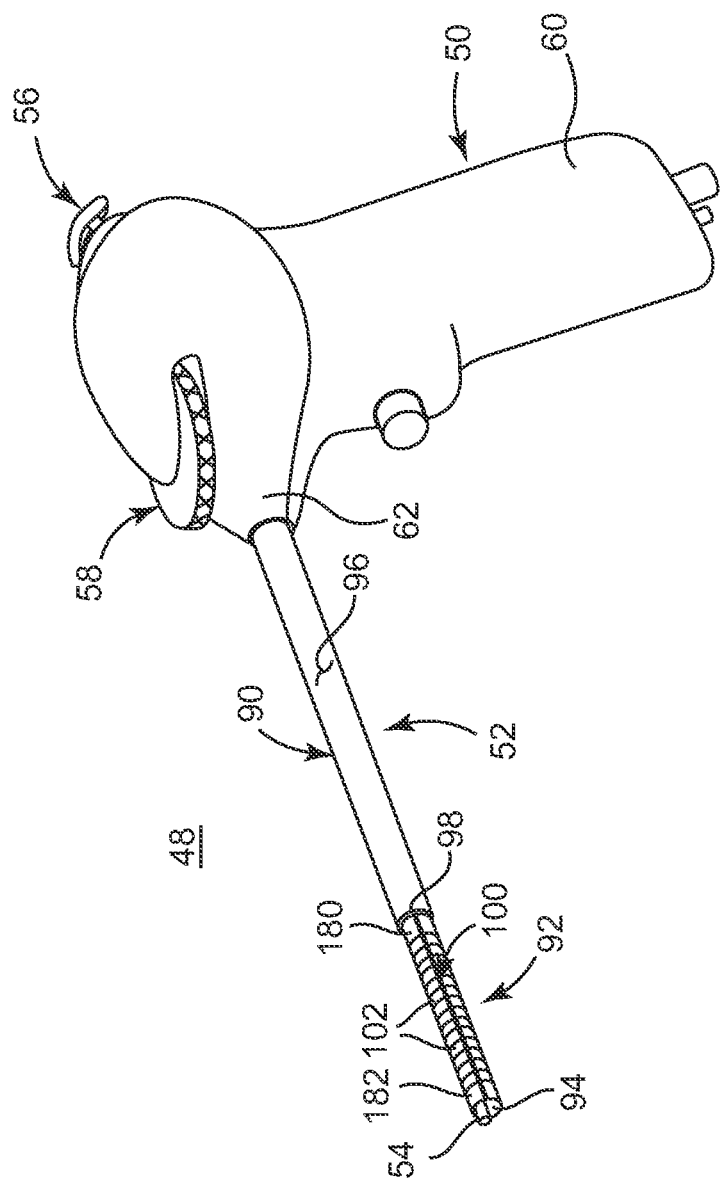
FIG. 2 is a side, perspective view of a surgical instrument useful with the systems of FIGS. 1A and 1B.

With the above general construction of the instrument 22 in mind, one acceptable configuration of a surgical biofilm removal instrument 48 is shown in FIG. 2. The instrument 48 includes a handle 50, an introducer 52, a nozzle 54, and irrigation and aspiration ducts (not shown). The instrument 48 can further optionally include a first actuator assembly 56 (referenced generally), and a second actuator assembly 58 (referenced generally). Details on the various components are provided below. In general terms, however, the handle 50 maintains the introducer 52 that is otherwise adapted for minimally invasive delivery to a surgical target site. In this regard, the introducer 52 maintains the nozzle 54 at a distal end thereof and through which pressurized flow of irrigant (not shown) is delivered in performing a biofilm removal procedure. With this in mind, the first actuator assembly 56 is operable by a user to effectuate bending of the introducer 52 (e.g., into or out of a plane of the view of FIG. 2). The second actuator assembly 58, and is operable by a user to effectuate movement or rotation of the nozzle 54 relative to the introducer 52.

The handle 50 can assume a variety of forms, and generally serves as a housing for various components of the instrument 48 and retains the introducer 52. In some embodiments, the handle 50 has a pistol grip-like shape, defining a grip portion 60 and a nose 62. The grip portion 60 is sized and shaped for grasping by a user's hand, whereas the nose 62 is adapted for connection to the introducer 52. Alternatively, other configurations are also acceptable (e.g., the handle 50 can assume other shapes or sizes differing from the pistol grip-like design illustrated).

Figure 3:
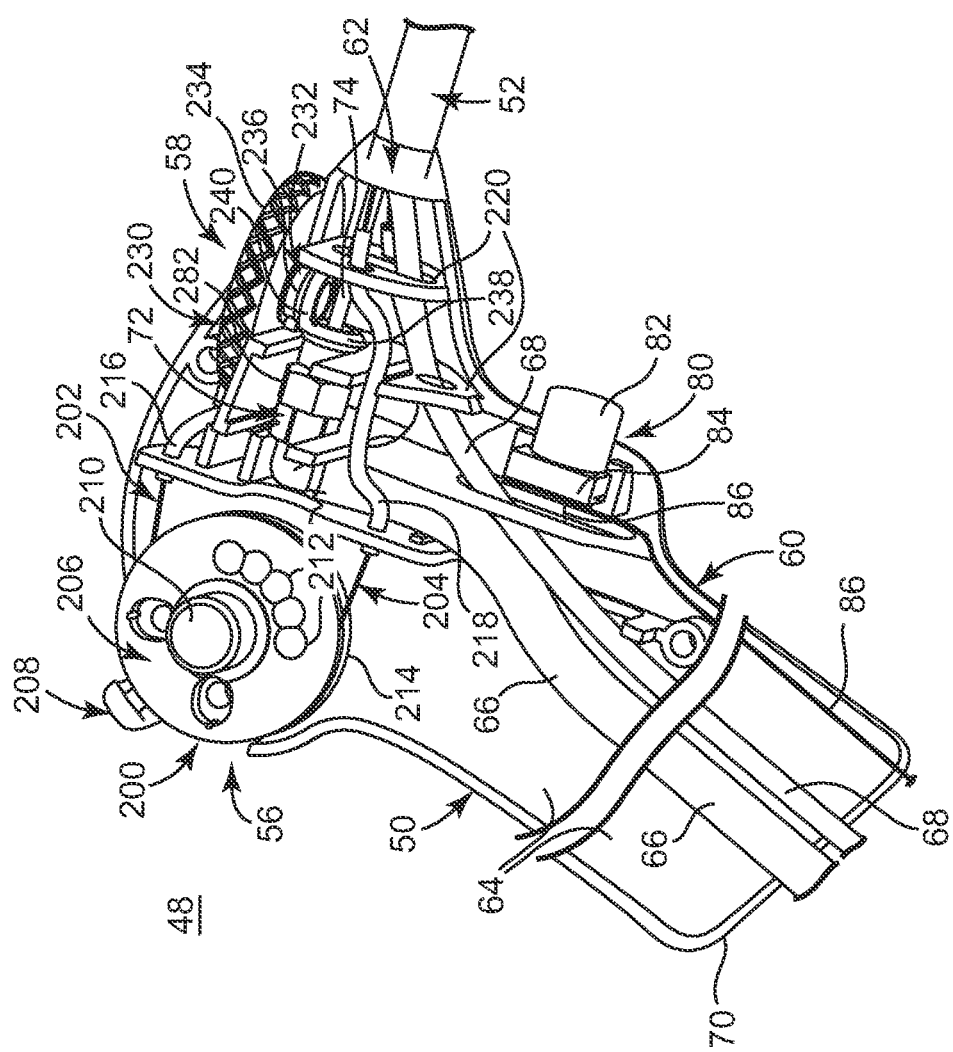
FIG. 3 is an enlarged view (with segments removed) of a portion of the instrument of FIG. 2.

With reference to FIG. 3, the handle 50 defines an interior 64 within which various components are housed. For example, the handle 50 can maintain irrigation tubing 66 and suction tubing 68. The irrigation tubing 66 and the suction tubing 68 extend from a trailing end 70 of the handle 50 and are directed toward the nose 62 and thus the introducer 52. In this regard, the irrigation tubing 66 can be provided as a continuation of the fluid connector 30 shown in FIG. 1A, whereas the suction tubing 68 can be provided as a continuation of the vacuum connector 32 of FIG. 1A. Alternatively, the handle 50 can include appropriate port configurations that provide a fluid connection between the irrigation tubing 66 and the fluid connector 30, and the suction tubing 68 and the vacuum connector 32, respectively. Regardless, the irrigation tubing 66 serves to direct irrigation fluid from the fluid source 24 (FIG. 1A) to the introducer 52, whereas the suction tubing 68 serves to direct aspirated fluid from the introducer 52 to the vacuum source 26 (FIG. 1A).

In some embodiments, the irrigation tubing 66 terminates at a fitting 72 that is otherwise provided as part of the second actuator assembly 58 as described below. In this regard, an irrigation delivery tube 74 extends from an opposite side of the fitting 72, with the fitting 72 establishing a fluid connection between the irrigation tubing 66 and the irrigation delivery tube 74. With this configuration, then, the irrigation delivery tube 74 extends into and through the introducer 52 and is fluidly connected to the nozzle 54 (FIG. 2). The irrigation tubing 66, the fitting 72, and the irrigation delivery tube 74 collectively form an irrigation duct through which irrigation fluid is delivered from the fluid source 24 (FIG. 1A) to the nozzle 54 as part of a biofilm removal procedure. Alternatively, a wide variety of other configurations for the irrigation duct are equally acceptable. For example, the irrigation duct can be a homogenous body (e.g., the irrigation tubing 66) extending directly through the handle 50 and the introducer 52.

The suction tubing 68 is shown in FIG. 3 as extending through the handle 50 and the introducer 52, and defines an aspiration duct through which fluid and other material at a distal end of the introducer 52 can be aspirated from the surgical site. Alternatively, however, one or more additional tubular components can also be provided in forming the aspiration duct.

In addition to the tubings 66, 68, the handle 50 further maintains a trigger assembly 80 that includes, in some embodiments, an activation member 82, a sensor 84 (drawn generally), and a connector 86. The activation member 82 extends externally from the grip portion 60 and is adapted to be actuated by a user (not shown), for example via a sliding interface relative to the grip portion 60. In this regard, the trigger assembly 80 can further include other components (not shown) that serve to bias the activation member 82 to the extended position (relative to the grip portion 60) as reflected in FIG. 3. Actuation of the activation member 82 thus entails a pushing force being applied thereon, sufficient to overcome a force of the biasing device to thus slide the activation member 82 inwardly; alternatively, other actuation arrangements are also acceptable. The sensor 84 is adapted to provide an output indicative of actuation (e.g., sliding movement) of the activation member 82, and thus can assume a variety of forms appropriate for sensing movement of the activation member 82. The connector 86, in turn, is adapted to carry, or transmit, the output from the sensor 84. Thus, the connector 86 can assume a variety of forms (e.g., tubing, wiring, etc.), and is connected (wired or wireless) to the controller 28 as shown by the connector 47 in FIG. 1A. For example, the connector 86 is connected to the sensor 84 and projects externally from the handle 50 via the trailing end 70.

Returning to FIG. 2, the introducer 52 has a generally elongated shape and is sized for minimally invasive bodily insertion, extending from the nose 62 of the handle 50. In this regard, the introducer 52 maintains the irrigation and aspiration ducts described above (hidden in FIG. 2), along a length thereof, and includes or defines a proximal portion 90 and a distal portion 92. The proximal portion 90 extends from the nose 60, whereas the distal portion 92 extends from the proximal portion 90, terminating at a distal end 94. As described in greater detail below, in some embodiments, the proximal portion 90 is characterized as being rigid, whereas the distal portion 92 is flexible or articulatable in allowing for user-controlled movement of the distal end 94 relative to the handle 50. Regardless, the nozzle 54 is maintained by the introducer 52 at the distal end 94.

The proximal portion 90 includes an outer housing 96 adapted to support various internal components, as well as the distal portion 92 relative to a leading side 98. In general terms, the housing 96 is tubular in nature, defining one or more lumens (not shown) within which various components (i.e., the suction tubing/aspiration duct 68 (FIG. 3), the irrigation delivery tube/irrigation duct 74 (FIG. 3), various wires (not shown), etc.) are disposed. In this regard, the irrigation and/or aspiration ducts can be in the form of separately formed tube(s) extending through the lumen(s) of the housing 96 as described above; alternatively, the lumen(s) of the housing 96 can serve as part of one or both of the irrigation and/or aspiration duct(s). In some embodiments, the housing 96 is formed of a fairly rigid, surgically safe material (e.g., plastic, stainless steel) although other materials are also acceptable.

As compared to the proximal portion 90, the distal portion 92 is flexible, with this flexibility being generated in some embodiments by an articulatable framework 100. The framework 100 is adapted to support various internal components (not shown) extending therethrough (e.g., the suction tubing/aspiration duct 68 (FIG. 3), the irrigation delivery tube/irrigation duct 74 (FIG. 3), wires, etc.), as well as the nozzle 54 maintained at the distal end 94. With this in mind, in some embodiments, the framework 100 is comprised of a plurality of links 102. Adjacent ones of the links 102 are pivotably or hingedly connected to one another in a manner allowing for relative movement as described below.

Figure 4:
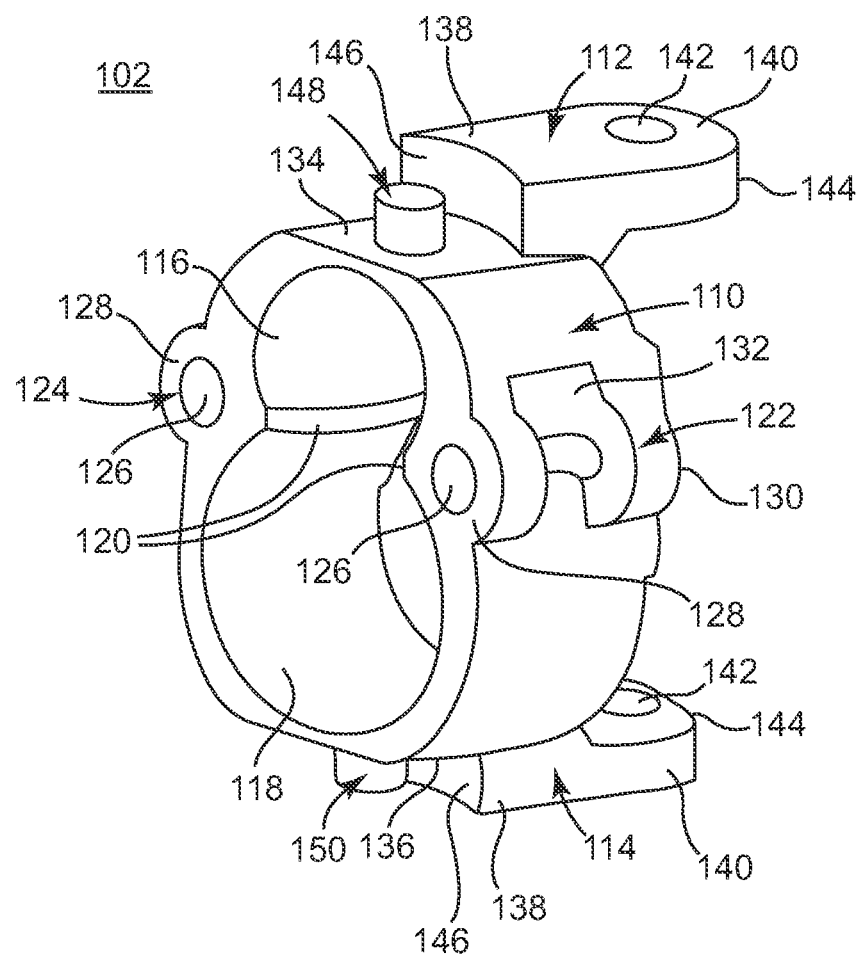
FIG. 4 is a perspective view of a link portion of the instrument of FIG. 2.

One acceptable embodiment of the links 102 is shown in greater detail in FIG. 4 (it being understood that the links 102 can have an identical construction). The link 102 includes a frame 110, a first flange 112, and a second flange 114. The frame 110 forms a first passage 116 and a second passage 118, with the passages 116, 118 extending longitudinally through the frame 110. The first passage 116 is sized to receive the irrigation delivery tube/irrigation duct 74 (FIG. 3), whereas the second passage 118 is sized to receive the suction tubing/aspiration duct 68 (FIG. 3). In this regard, while the first and second passages 116, 118 are open relative to one another within the frame 110, a partial shoulder 120 can be formed, adapted to slidably capture the irrigation delivery tube/irrigation duct 74 relative to the first passage 116, and the suction tubing/aspiration duct 68 relative to the second passage 118. Alternatively, however, a singular passage can be defined by the frame 110 (e.g., the shoulder 120 can be eliminated), or the passages 116, 118 can be closed relative to one another. Even further, in other embodiments, a multiplicity of passages can be formed by or within the frame 110.

Regardless of the number and/or construction of the passages 116, 118, the frame 110 further includes first and second ribs 122, 124 at opposite sides thereof. The ribs 122, 124 are generally defined as radial projections relative to the frame 110, and can be located adjacent the partial shoulder 120 so as to minimize an overall width of the link 102. Regardless, each of the ribs 122, 124 forms or defines a longitudinal bore 126 extending from a first side 128 to a second side 130 (referenced generally) of the frame 110. As shown in FIG. 4, the ribs 122, 124 can be constructed such that the bore 126 is radially open along a slot 132. Regardless, the bores 126 are each sized to slidably receive a wire (not shown) associated with the first actuator assembly 56 (FIG. 2) as described below.

The first and second flanges 112, 114 project from opposite ends of the frame 110. For example, with respect to the orientation of FIG. 4, the first flange 112 projects a "top" end 134 of the frame 110, whereas the second flange 114 projects from a "bottom" end 136 of the frame 110 (it being understood that the link 102 can be oriented in any direction, such that the terms "top" and "bottom" are in no way limiting). With these conventions in mind, each of the flanges 112, 114 includes or defines a fixed end 138 and a free end 140. The fixed end 138 is contiguous with the corresponding end 134 or 136 of the frame 110, whereas the free end 140 is spaced from the frame 110 (i.e., positioned or located away from the second side 130 of the frame 110). The flanges 112, 114 each include or form a transverse aperture 142 extending through a thickness thereof, located adjacent the free end 140. Further, the free end 140 forms a convex curved surface 144, whereas the fixed end 138 forms a corresponding, concave curved surface 146. As described in greater detail below, the convex and concave surfaces 144, 146 have a corresponding or matched shape, such that upon assembly of the link 102 to a second link (not shown), a translatable relationship is established. Finally, the link 102 includes a first pin 148 and a second pin 150. The first pin 148 extends transversely from the top end 134 of the frame 110, whereas the second pin 150 extends transversely from the bottom end 136. The pins 148, 150 are, in some embodiments, identically constructed, and are sized to be rotatably received within the aperture 142 associated with the corresponding flange 112 or 114 of a separate one of the links 102.

Figure 5:
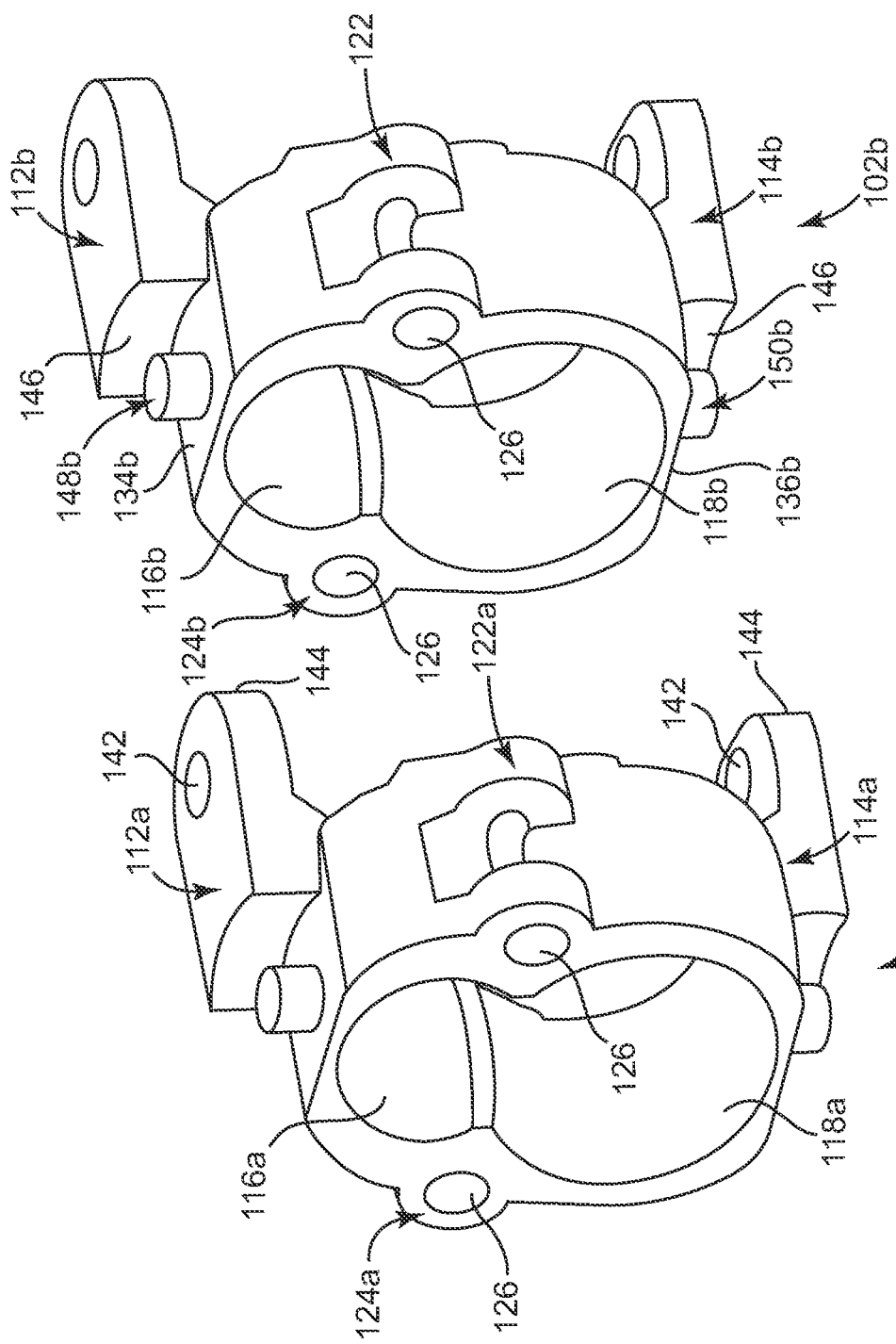
FIG. 5 is an exploded, perspective view illustrating assembly of the links of FIG. 4.

With the above construction in mind, FIG. 5 illustrates, in exploded form, exemplary assembly of a first one of the links 102a to a second one of the links 102b. As a point of reference, for ease of explanation, the element numbering identified above with respect to the link 102 of FIG. 4 are designated with an "a" or "b" in FIG. 5, corresponding to the link 102a or 102b being described. With this in mind, the links 102a, 102b are assembled to one another such that the first flange 112a of the first link 102a is assembled to the top end 134b of the second link 102b, and the second flange 114a is assembled to the bottom end 136b. More particularly, the first pin 148b of the second link 102b is rotatably received within the aperture 142 of the first flange 112a of the first link 102a, whereas the second pin 150b is rotatably received within the aperture 142 of the second flange 114a. In this regard, the convex surface 144 of the first flange 112a of the first link 102a mates with the concave surface 146 of the first flange 112b of the second link 102b such that the first flange 112a can rotate (about the first pin 148b) relative to the first flange 112b (i.e., the convex surface 144 of the first link's flange 112a can translated along or relative to the concave surface 146 of the second link's flange 112b, and vice-versa). A similar relationship is established between the second flanges 114a, 114b.

Upon assembly, the first ribs 122a, 122b are longitudinally aligned, as are the second ribs 124a, 124b. With this arrangement, wires (not shown) can continuously extend through the aligned ribs 122a, 122b and 124a, 124b as described below. Similarly, the first passages 116a, 116b are aligned for receiving the irrigation duct 74 (FIG. 3). The second passages 118a, 118b are aligned for receiving the aspiration duct 66 (FIG. 3).

Figure 6:
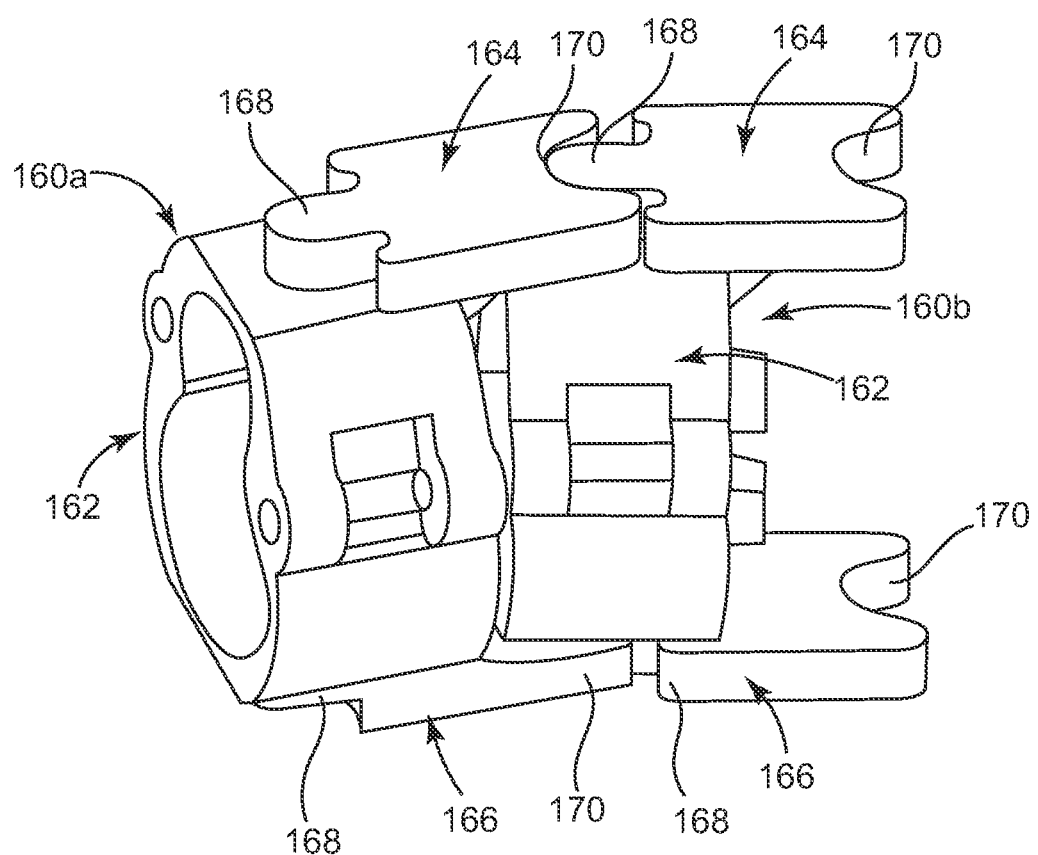
FIG. 6 is a perspective view of two alternative links useful with the instrument of FIG. 2 upon final assembly.

The construction of the links 102 (including the links 102a, 102b) described above is but one acceptable configuration in accordance with principles of the present disclosure. For example, FIG. 6 illustrates an alternative configuration of a link 160 useful with the present disclosure. The link 160 (two of which (160a, 160b) are shown in FIG. 6) again includes a frame 162 and opposing flanges 164, 166. Each of the flanges 164, 166 includes a convex side 168 and a concave side 170, with the convex side 168 configured to pivotably interface with the concave side of the flange 164 or 166 of a second, adjacent link (e.g., the concave side of the flange 164 of the first link 160a receives the convex side of the flange 164 of the second link 160b). Unlike the hinge joint arrangement of FIG. 5, the link 160 of FIG. 6 incorporates an open pivot-type interface between adjacent links 160a, 160b. With this configuration, in instances of elevated loading (e.g., attempting to overtly pivot or rotate adjacent links 160a, 160b relative to one another), the pivot joint established between adjacent ones of the flanges 164 or 166 can flex out of position and spring back when the load is removed.

Returning to FIG. 2, regardless of an exact construction, the framework 100 is assembled to the leading side 98 of the proximal portion 90 so as to define a proximal link 180 and a distal link 182. User-controlled movement (or bending) of the distal portion 92 is described in greater detail below with reference to the first actuator assembly 56 (referenced generally in FIG. 2). Regardless, the distal link 182 terminates at or defines the distal end 94, and maintains the nozzle 54 as best shown in FIG. 7. In addition, the second passage 118 of the distal link 182 is longitudinally open relative to an exterior of the introducer 52, and thus defines an aspiration inlet 184 that is otherwise fluidly connected to the aspiration duct described above (not shown or hidden in FIG. 7, but can be the suction tubing 68 (FIG. 3) otherwise extending through the introducer 52). To this end, the aspiration duct can project distally through and beyond the distal link 182, with the distal end of the aspiration duct defining the aspiration inlet 184.

The nozzle 54 can assume a variety of forms, but in some embodiments is configured to generate a fan-like spray pattern, and is rotatably maintained by, or assembled to, the distal link 182. As a point of reference, in accordance with some aspects of the present disclosure, the biofilm removal surgical instrument 22 (FIG. 1A) is provided to mechanically disrupt biofilms with a fluid stream as produced through the nozzle 54. In this regard, while the nozzle 54 can be a simple orifice-type nozzle, it has been surprisingly found that a fan spray-type nozzle configuration can provide unexpected benefits in the context of biofilm removal. An orifice nozzle produces a focused stream approximately equal to the diameter of the orifice. This, in turn, produces mechanical disruption on a relatively small area of tissue during use. To effectuate biofilm removal over a larger area, then, an orifice-type nozzle likely must then be articulated in space to treat other areas. With the one configuration of FIG. 7, however, the nozzle 54 is a fan spray-type nozzle that produces mechanical disruption on a "line" of tissue. When the nozzle 54 is rotated about its axis (as described below), this line can then sweep out a comparatively large area of tissue.

With the above in mind, the nozzle 54 can be a tubular-type body defining a base end 186 (referenced generally) assembled to the introducer 52, and an opposite leading, hemispherical end 188 at which a V-cut 190 is made. In some embodiments, and as shown in FIG. 7, the V-cut 190 is formed to extend along a side 192 of the nozzle 54 so as to produce a side-looking spray pattern (and thus cover more area with rotation of the nozzle 54 as described below). Alternatively, the V-cut 190 can be centrally formed relative to an axis of the nozzle 54. Regardless, it has been found that parameters that control the shape of the fan spray pattern generated by the nozzle 54 are the angle of the V-cut 190, and an inner diameter of the nozzle 54 orifice (not shown). With these parameters in mind, it has surprisingly found that a nozzle configuration adapted to operate upon a supply flow rate of 6 mL/sec in generating a spray force equivalent to the force found with a 0.03 inch orifice nozzle at distances up to 1.3 inch can be achieved where the V-cut 190 defines an included angle in the range of 25°-100° and an inner diameter opening size in the range of 0.0001-0.0007 inch$^2$. Alternatively, however, a wide variety of other configurations for the nozzle 54 are also acceptable. Regardless, the nozzle 54 is assembled to the introducer 52 such that the leading end 188 of the nozzle 54 projects distally beyond the distal end 94 of the introducer 52 such that the spray pattern generated by or through the V-cut 190 is not impacted by the introducer 52.

Returning to FIGS. 2 and 3, the first actuator assembly 56 is configured to provide user-controlled movement or articulation of the distal portion 92, and includes, in some embodiments, an actuator 200, a first wire 202, and a second wire 204. The first and second wires 202, 204 are assembled to the actuator 200, and extend to the introducer 52 as described below. With this configuration, movement of the actuator 200 is translated onto the wires 202, 204, that in turn effectuate movement of the introducer 52, and in particular the distal portion 92, relative to the handle 50.

In some embodiments and with specific reference to FIG. 3, the actuator 200 includes a wheel 206 and a control knob 208. The wheel 206 is rotatably assembled to the handle 50, with the control knob 208 extending radially from the wheel 206 and, upon final assembly, projecting externally relative to the handle 50. With this configuration, then, the control knob 208 is available for being acted upon by a user (not shown) otherwise grasping the handle 50, such as by the user's thumb. Regardless, the wheel 206 is rotatable about a center point 210 relative to the handle 50, and can include or form one or more indentations 212 in some embodiments. The indentations 212 are each sized to releasably capture a corresponding control body (not shown) otherwise carried by the handle 50 in selectively "locking" the wheel 206 relative to the handle 50. For example, a ball biased against the wheel 206 can be provided and sized to selectively nest within a corresponding one of the indentations 212. Alternatively, a wide variety of other locking-type mechanisms can be employed such that the indentations 212 can assume other forms and/or can be eliminated. In yet other embodiments, the first actuator assembly 56 does not include a locking mechanism.

The first wire 202 and the second wire 204 are each separately affixed to the wheel 206, for example extending within a circumferential groove 214 (referenced generally) formed by the wheel 206. As shown, the wires 202, 204 each extend from the wheel 206 toward the nose 62 of the handle 50. To this end, the instrument 48 can further include first and second wire guides 216, 218 that direct the wires 202, 204, respectively, along an interior of the handle 50 so as to avoid undesired contact with other components of the instrument 48. In this regard, the wire guides 216, 218 can be supported by one or more walls 220 assembled or provided within the handle 50. Regardless, the wires 202, 204 extend through the nose 62 and into the introducer 52 as described below. Relative to the upright orientation of FIG. 2, in some embodiments, the first actuator assembly 56 is constructed such that the wires 202, 204 transition from a vertical orientation or relationship at the wheel 206 to a horizontal orientation or relationship at the nose 62/introducer 52. That is to say, relative to a point of assembly with the wheel 206, the first wire 202 is "above" the second wire 204; conversely, as positioned at the nose 62/introducer 52, the first and second wires 202, 204 are generally horizontally aligned. Alternatively, however, a wide variety of other constructions are also acceptable including, for example, the wires 202, 204 extending linearly through the housing 50.

With additional reference to FIG. 2, the wires 202, 204 (hidden in FIG. 2) extend through the proximal portion 90 and the distal portion 92 of the introducer 52. Relative to the proximal portion 90, for example, the wires 202, 204 can be slidably maintained within a corresponding lumen defined thereby; can be commonly maintained within a single lumen; etc. Regardless, the distal portion 92 is also configured to facilitate extension of the wires 202, 204 to the distal end 94. For example, and as previously described with respect to FIG. 4, the links 102 include the opposed ribs 122, 124, each of which forms the longitudinal bore 126. The longitudinal bores 126 are sized to slidably receive a respective one of the wires 202 or 204, with respective ones of the bores 126 being aligned with a corresponding one of the bores 126 of an adjacent link 102. A wide variety of other constructions are also acceptable. Regardless, the wires extend to the distal end 94 of the distal portion 92, and are individually attached thereto. For example, each of the wires 202, 204 is affixed to the distal link 182.

Figure 9:
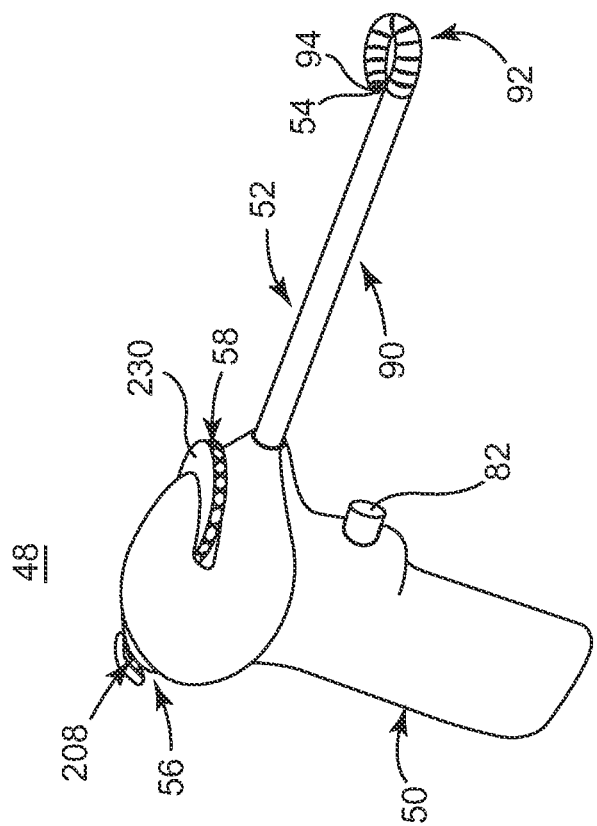
FIG. 9 is a perspective view of the instrument of FIG. 2, illustrating articulation of an introducer portion thereof.
Figure 8:
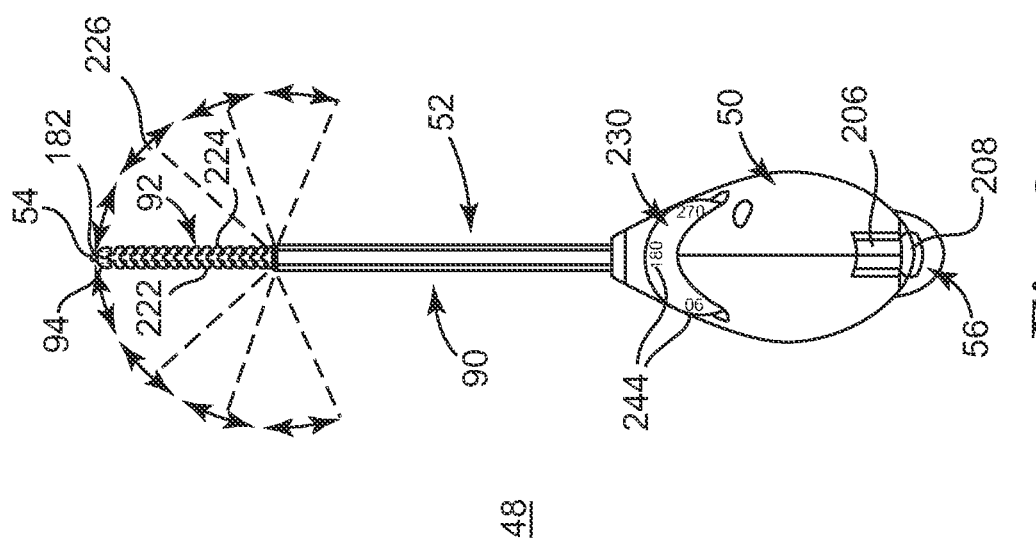
FIG. 8 is a top view of the instrument of FIG. 2.

As schematically represented in FIG. 8, then, the first wire 202 (referenced generally) extends along a first side 222 of the distal portion 92, whereas the second wire 204 (referenced generally) extends along an opposite, second side 224. With this construction, and with additional reference to FIG. 3, rotation of the wheel 206 imparts a pulling force onto one of the first or second wires 202, 204, and a corresponding pushing force onto the other of the wires 202, 204. For example, relative to the orientation of FIG. 3, rotation of the wheel 206 in a counter-clockwise direction (e.g., a user placing an upward force onto the control knob 208) imparts a pulling force onto the first wire 202 and a pushing force onto the second wire 204. These forces, in turn, are translated via the wires 202, 204 onto the distal link 182, creating a force urging the first side 222 to move "toward" the handle 50 (and the second side 224 to move "away" from the handle 50). The articulating or pivotable relationship of the links 102 otherwise comprising the articulatable framework 100 allows the distal portion 92 to flex or articulate in response to these pushing/pulling forces. Thus, as shown in FIG. 9, the distal portion 92 will bend or flex in response to the user-placed force imparted upon the control knob 208. Notably, the suction tubing/aspiration duct 68 (FIG. 3) and the irrigation delivery tube/irrigation duct 74 (FIG. 3) (otherwise extending through or along the distal portion 92) exhibit sufficient flexibility so as to not impede this desired movement, yet sufficient structural integrity to not kink or collapse when flexed. Regardless, the first actuator assembly 56 affords the user the ability to dictate a desired position or angle of attack of the distal end 94, and thus the nozzle 54 retained thereby, via operation of the control knob 208. This, in turn, allows selectively adjusting the nozzle 54 through, and independently maintaining the nozzle 54 at, a plurality of angles of attack 226 as shown in FIG. 8. The suction tubing/aspiration duct 68, and in particular the aspiration inlet 184 (FIG. 7), is similarly selectively directed through different angles as desired.

A rotational position of the nozzle 54 (and the V-cut 190 and thus the line spray pattern generated thereby) can similarly be controlled or altered by a user via the second actuator assembly 58. With specific reference to FIG. 3, the second actuator assembly 58 includes a control wheel 230, a geared arrangement 232, and the fitting 72 as previously described. The control wheel 230 is rotatably maintained by the handle 50 such that at least a segment 234 thereof is exteriorly exposed regardless of a rotational position. In some embodiments, the control wheel 230 is positioned adjacent the nose 62, and is located to be easily acted upon by a user otherwise grasping the handle 50 (either by a finger of a hand grasping the grip portion 60, or by a second hand of the user). The geared arrangement 232 is associated with the control wheel 230, and in some embodiments includes first and second gears 236, 238. The first gear 236 includes a beveled surface 240 and is coaxially affixed to the control wheel 230. The second gear 238 includes or forms a complementary beveled surface 242 (referenced generally in FIG. 3) such that the first and second gears 236, 238 are in meshed engagement. Further, the second gear 238 is assembled to the fitting 72 as well as the irrigation delivery tube 74. With rotation of the control wheel 230, then, the first gear 236 rotates the second gear 238 in a perpendicular plane, with this rotational movement being imparted onto the irrigation delivery tube 74. As previously described, the irrigation delivery tube 74 is, or forms part of, the irrigation duct that extends through the introducer 52, and is fluidly affixed to the nozzle 54. As a result, the nozzle 54 (FIG. 7) rotates with rotation of the irrigation delivery tube 74/second gear 238. In some embodiments, the fitting 72 is a swivel-type fitting such that the second gear 238 maintains meshed engagement with the first gear 236 with articulating movement of the introducer 52 as previously described with operation of the first actuator assembly 56.

It will be understood that the above description of the second actuator assembly 58 is but one acceptable design for effectuating user-controlled rotation of the nozzle 54. Thus, the control wheel 230/geared arrangement 232 can be replaced by or include other components. In some embodiments, however, and with specific reference to FIG. 8, the control wheel 230 includes indicia 244 along an exterior surface thereof. The indicia 244 is at least partially viewable external the handle 50, and provides a user with a visual indication of a rotational position of the nozzle 54 relative to the introducer 52, and in particular, the line-type spray pattern produced thereby. Thus, for example, the indicia 244 can include a numerical indication of an angular orientation of the spray pattern being generated by the nozzle 54. Alternatively, however, the indicia 244 can be eliminated.

With the above explanations in mind, upon final assembly, the biofilm removal surgical instrument 48 is constructed to deliver a focused, pressurized spray or flow of fluid from the distal end 94 of the introducer 52 via the nozzle 54. In this regard, the supply of irrigation fluid is provided via the irrigation tubing/irrigation duct 66 (FIG. 3). Similarly, aspiration at the aspiration inlet 184 (FIG. 7) is provided via the suction tubing/aspiration duct 68 (FIG. 3). The spatial, angular orientation of the distal end 94, and thus of the nozzle 54, can be selected and altered by a user via the first actuator assembly 56 (and in particular manipulation of the control knob 208). Similarly, a spatial orientation of the line spray pattern generated by the nozzle 54 can be "rotated" by a user via the second actuator assembly 58 (and in particular manipulation of the control wheel 230).

Figure 10:
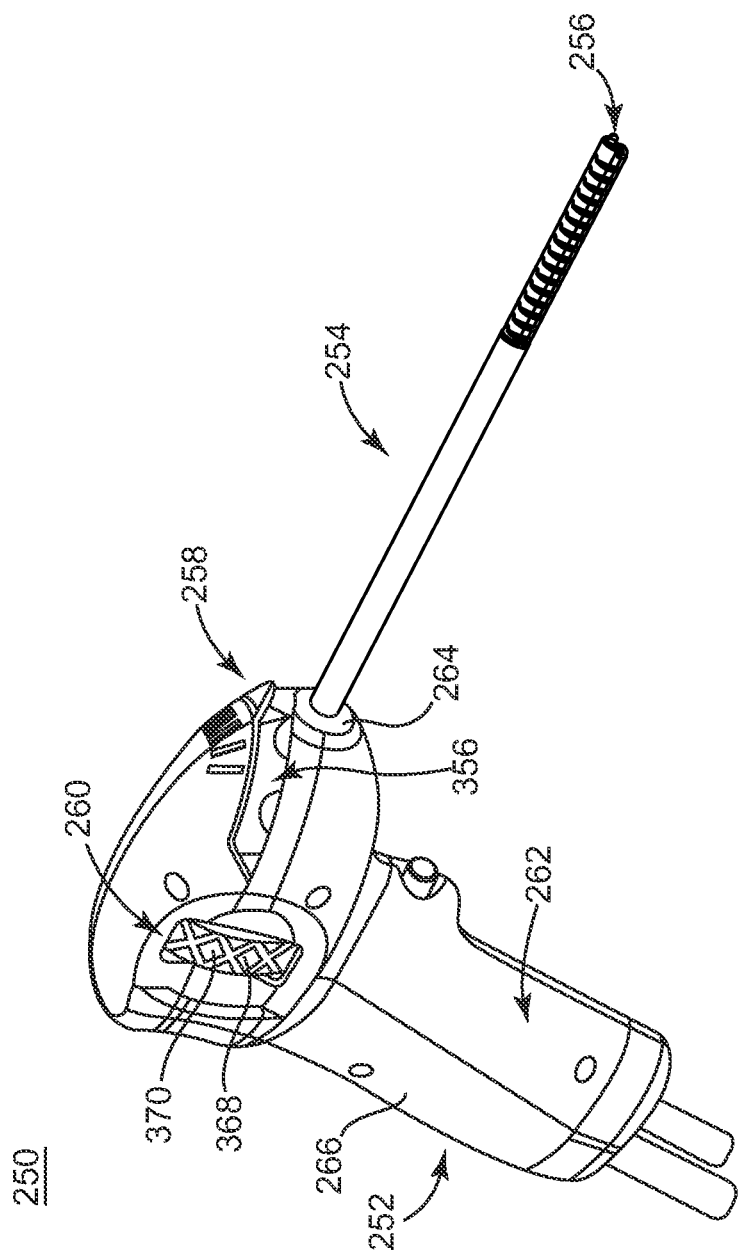
FIG. 10 is a perspective view of another surgical biofilm removal instrument in accordance with principles of the present disclosure and useful with the systems of FIGS. 1A and 1B.

Another example of a biofilm removal surgical instrument 250 in accordance with aspects of the present disclosure and useful with the systems 20, 20' (FIGS. 1A, 1B) is shown in FIG. 10. The instrument 250 includes a handle 252, an introducer 254, a nozzle 256 (referenced generally) and irrigation and aspiration ducts (not shown). The instrument 250 can further optionally include a first actuator assembly 258 (referenced generally), and a second actuator assembly 260 (referenced generally). Details on the various components are provided below. In general terms, however, the handle 252 maintains the introducer 254 that is otherwise adapted for minimally invasive delivery to a surgical target site. In this regard, the introducer 254 maintains the nozzle 256 at a distal end thereof and through which pressurized flow of irrigant (not shown) is delivered in performing a biofilm removal procedure. The first actuator assembly 258 is operable by a user to effectuate bending of the introducer 254, whereas the second actuator assembly 260 is operable to effectuate movement or rotation of the nozzle 256 relative to the introducer 254.

The handle 252 is akin to the handle 50 (FIG. 2) previously described, generally serving as a housing for various components of the instrument 250 and retains the introducer 254. As with the handle 50, the handle 250 has a pistol grip-like shape, defining a grip portion 262 and a nose 264. The grip portion 252 is sized and shaped for grasping by a user's hand, whereas the nose 264 is adapted for connection to the introducer 254.

Figure 11:
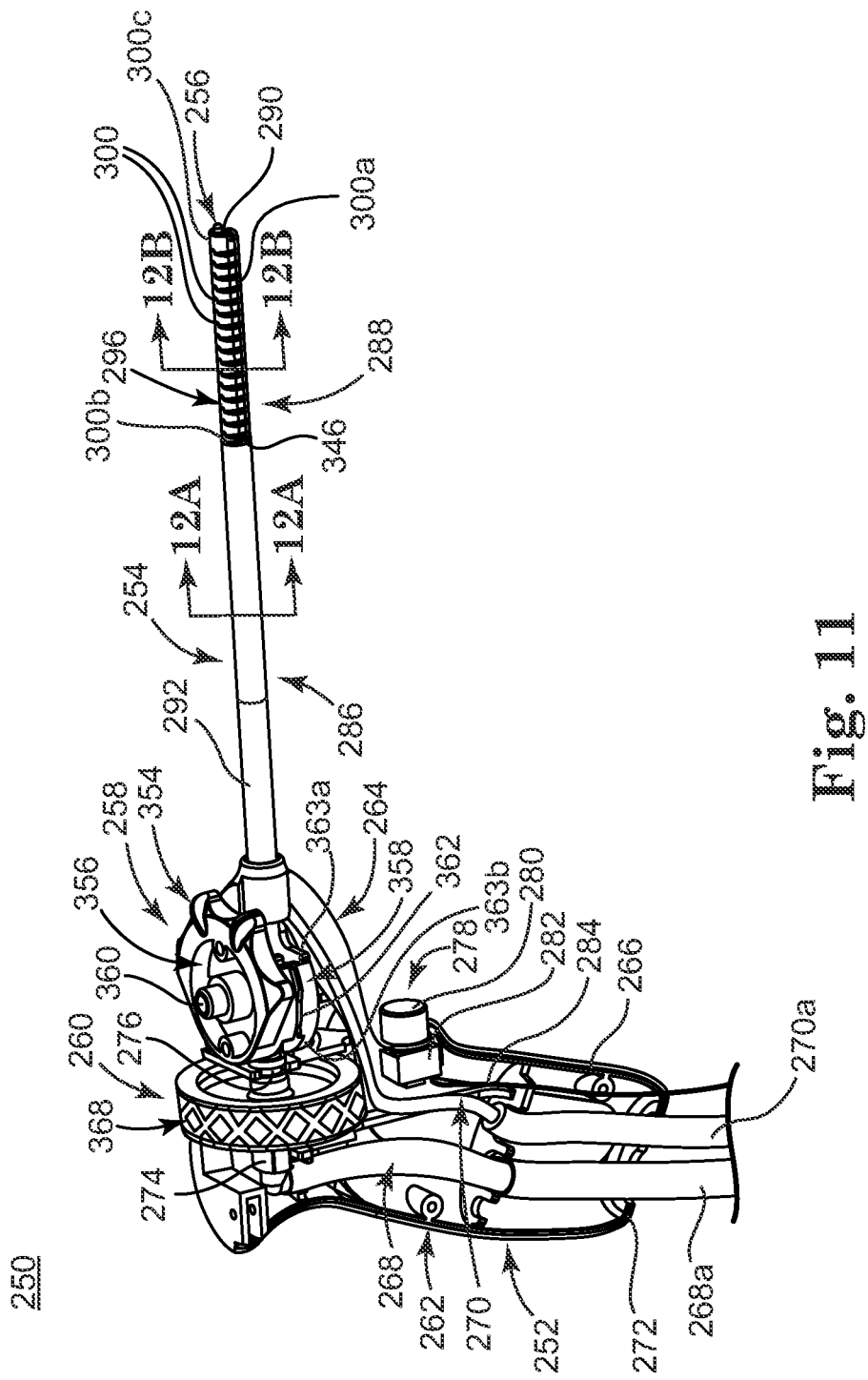
FIG. 11 is an enlarged view (with a portion removed) of the surgical instrument of FIG. 10.

With additional reference to FIG. 11 (in which a portion an outer housing or shell 266 of the handle 252 is removed to better illustrate internal components thereof), the handle 252 maintains irrigation tubing 268 and suction or aspiration tubing 270. The irrigation tubing 268 and the suction tubing 270 extend from a trailing end 272 of the handle 252 and are directed toward the nose 264 and thus the introducer 254. As a point of reference, FIG. 11 reflects that the irrigation tubing 268 and the suction tubing 270 optionally can taper in diameter from a proximal segment 268a, 270a, respectively, to better accommodate one construction of the handle 252. Further, the irrigation tubing 268 can be provided as a continuation of the fluid connector 30 shown in FIG. 1A, whereas the suction tubing 270 can be provided as a continuation of the vacuum connector 32 of FIG. 1A. Alternatively, the handle 252 can include appropriate port configurations that provide a fluid connection between the irrigation tubing 268 and the fluid connector 30, and the suction tubing 270 and the vacuum connector 32, respectively. Regardless, the irrigation tubing 268 serves to direct irrigation fluid from the fluid source 24 (FIG. 1A) to the introducer 254, whereas the suction tubing 270 serves to direct aspirated fluid from the introducer 254 to the vacuum source 26 (FIG. 1A).

In some configurations, the irrigation tubing 268 terminates at a fitting 274 that is otherwise provided as part of the second actuator assembly 260 as described below. In this regard, a first irrigant delivery tube 276 (referenced generally) extends from an opposite side of the fitting 274, with the fitting 274 establishing a fluid connection between the irrigation tubing 268 and the first irrigant delivery tube 276. The first irrigant delivery tube 276, in turn, extends into and through the introducer 254, and is fluidly connected to the nozzle 256 (as described below) in collectively establishing or forming an irrigation duct through which irrigation fluid is delivered from the fluid source 24 (FIG. 1A) to the nozzle 256 as part of a biofilm removal procedure. For example, the first irrigant delivery tube 276 can be connected to a second irrigant delivery tube (shown in FIG. 12B at 298) that in turn is fluidly connected to the nozzle 256. Alternatively, a wide variety of other configurations for the irrigation duct are equally acceptable. For example, the irrigation duct can be a homogenous body (e.g., the irrigation tubing 268) extending directly through the handle 252 and the introducer 254 to the nozzle 256.

The suction tubing 270 is shown in FIG. 11 as extending through the handle 252 and the introducer 254, and defines an aspiration duct through which fluid and other material at a distal end of the introducer 254 can be aspirated from the surgical site. Alternatively, however, one or more additional tubular components can also be provided in forming the aspiration duct.

The handle 252 further maintains a trigger assembly 278 that is akin to the trigger assembly 80 (FIG. 3) previously described. Thus, the trigger assembly 278 includes an activation member 280, a sensor 282 (drawn generally), and a connector 284. Reference is made to the above description of the trigger assembly 80 for construction and operation of the trigger assembly 278. In general terms, the connector 284 is adapted to carry, or transmit, the output from the sensor 282, and is connected (wired or wireless) to the controller 28 by the connector 47 as shown in FIG. 1A.

The introducer 254 is akin to the introducer 52 (FIG. 2) previously described and extends from the nose 264. In this regard, the introducer 254 maintains the irrigation and aspiration ducts described above along a length thereof, and includes or defines a proximal portion 286 and a distal portion 288. The proximal portion 286 extends from the nose 264, whereas the distal portion 288 extends from the proximal portion 286, terminating at a distal end 290. The proximal portion 286 is characterized as being relatively rigid, whereas the distal portion 288 is flexible or articulatable (relative to a rigidity of the proximal portion 286) in allowing for user-controlled movement of the distal end 290 relative to the handle 252. Regardless, the nozzle 256 is maintained by the introducer 254 at the distal end 290.

Figure 12A:
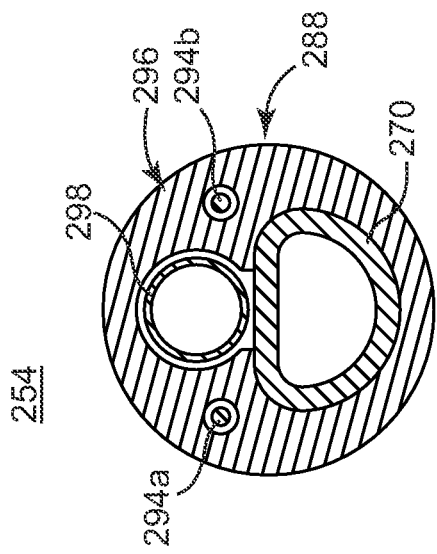
FIG. 12A is a cross-sectional view of an introducer portion of the instrument of FIG. 11, taken along the lines 12A-12A.

As with the introducer 52 of FIG. 2, the proximal portion 286 includes an outer housing 292 supporting various internal components including, for example, the irrigant delivery tube/irrigation duct 276, the suction tubing/aspiration duct 270, and pull wires 294a, 294b as shown in FIG. 12A. In this regard, the irrigation and/or aspiration ducts can be in the form of separately formed tube(s) extending through a single lumen 295 of the housing 292 as shown. Alternatively, the housing 292 can form multiple lumens within which the suction tubing 270, the irrigant delivery tube 276, and the pull wires 294a, 294b are separately maintained. Along these same lines, the lumen(s) of the housing 292 can serve as part of one or both of the irrigation and/or aspiration duct(s). As a point of reference, the pull wires 294a, 294b are described in greater detail below with respect to the first actuator assembly 258 (FIG. 10).

Figure 12B:
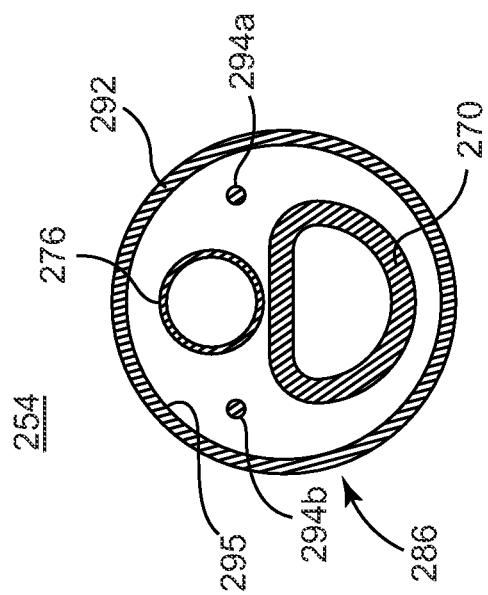
FIG. 12B is a cross-sectional view of an introducer portion of the instrument of FIG. 11, taken along the lines of 12B-12B.

Returning to FIG. 11, the distal portion 288 is flexible, with this flexibility being imparted in some embodiments by an articulatable framework 296. As shown in FIG. 12B, the framework 296 is adapted to support various internal components extending therethrough, including the suction tubing 270 and the pull wires 294a, 294b. In some configurations, the distal portion 288 includes a second irrigant delivery tube 298. With additional reference to FIG. 12A, the second irrigant delivery tube 298 is fluidly connected to the first irrigant delivery tube 276, with the second irrigant delivery tube 298 being more flexible than the first irrigant delivery tube 276. For example, in some embodiments, the first irrigant delivery tube 276 (otherwise extending through the proximal portion 286 and into the handle 252) is comprised of a stainless steel material, whereas the second irrigant delivery tube 298 is a braided Pebax™ tube. As described below, a flexibility of the second irrigant delivery tube 298 is conducive to articulation of the distal portion 288. Conversely, a rigidity of the first irrigant delivery tube 276 promotes or facilitates desired rotation of the nozzle 256 relative to the introducer 254. With this embodiment, then, the irrigant delivery tubes 276, 298 combine to define at least a portion of the irrigation duct described above. Once again, however, other constructions are also acceptable in establishing a fluid connection to the nozzle 256.

As with previous embodiments, the framework 296 is comprised of a plurality of links 300 including intermediate links 300a, a proximal link 300b, and a distal link 300c. Adjacent ones of the links 300 are pivotably or hingedly connected to one another in a manner allowing for relative movement as described below.

Figure 13A:
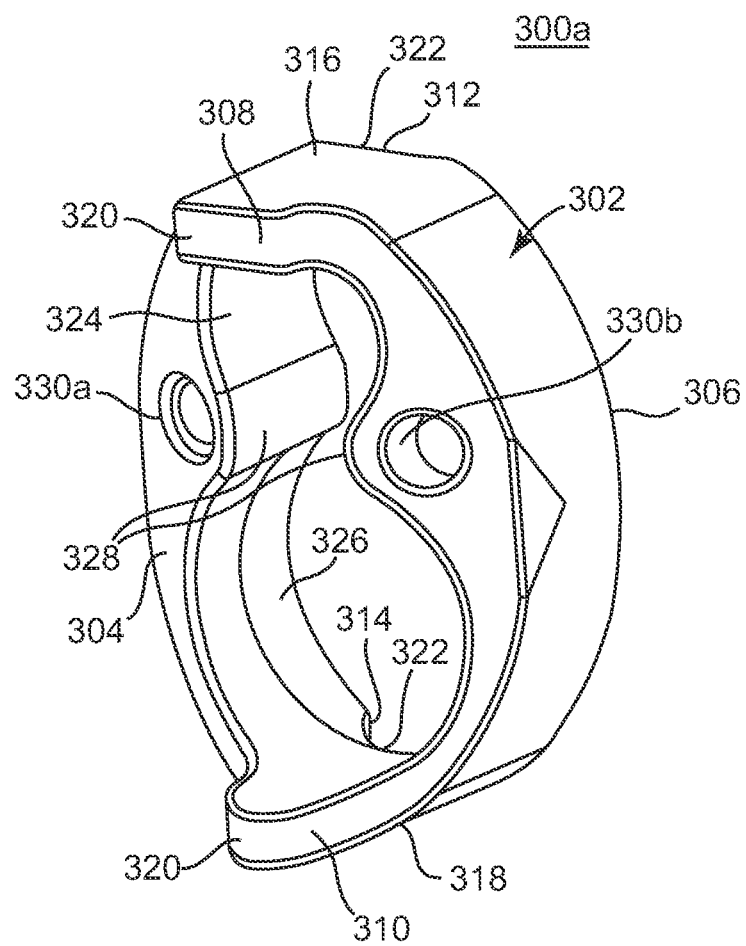
FIG. 13A is an enlarged, perspective view of an introducer intermediate link of the instrument of FIG. 11.

With additional reference to FIG. 13A, each of the intermediate links 300a, includes a frame 302 defining a first side 304 and a second side 306. First and second flanges 308, 310 are formed along the first side 304, whereas first and second grooves 312, 314 are formed along the second side 306. The first and second flanges 308, 310 are, in some embodiments, identical as are the grooves 312, 314, with the flange/groove pairs 308/312, 310/314 being formed at opposite ends 316, 318 respectively, of the frame 302. In this regard, the flanges 308, 310 are formed as longitudinal extensions relative to the frame 302, terminating at a curved or convex surface 320. The first and second grooves 312, 314, in turn, define a curved or concave surface 322. As described in greater detail below, the convex and concave surfaces 320, 322 have a corresponding or matched shape, such that upon assembly of the link 300a to a second link (not shown), a meshed, translatable relationship is established.

The frame 302 further forms first and second passages 324, 326. The first passage 324 is sized to receive the irrigation duct (e.g., the second irrigant delivery tube 298 of FIG. 12B), whereas the second passage 326 is sized to receive the aspiration duct (e.g., the suction tubing 270 of FIG. 12B). In this regard, while the first and second passages 324, 326 are open relative to one another, with the one embodiment of FIG. 13A, a partial shoulder 328 can be formed, adapted to slidably capture the irrigation duct/irrigant tube 298 relative to the first passage 324, and the aspiration duct/suction tubing 270 relative to the second passage 326. Alternatively, however, a singular passage can be defined by the frame 302 (e.g., the shoulder 328 can be eliminated), or the passages 324, 326 can be closed relative to one another. Even further, in other embodiments, a multiplicity of discrete passages can be formed by or within the frame 302.

Finally, the frame 302 forms or defines first and second longitudinal bores 330a, 330b. The bores 330a, 330b are formed in an opposing manner relative to the frame 302, and are optionally located adjacent the partial shoulder 328 so as to minimize an overall width of the link 300a. In this regard, the bores 330a, 330b are sized to slidably receive one of the pull wires 294a, 294b (FIG. 12B) as described below.

Figure 13B:
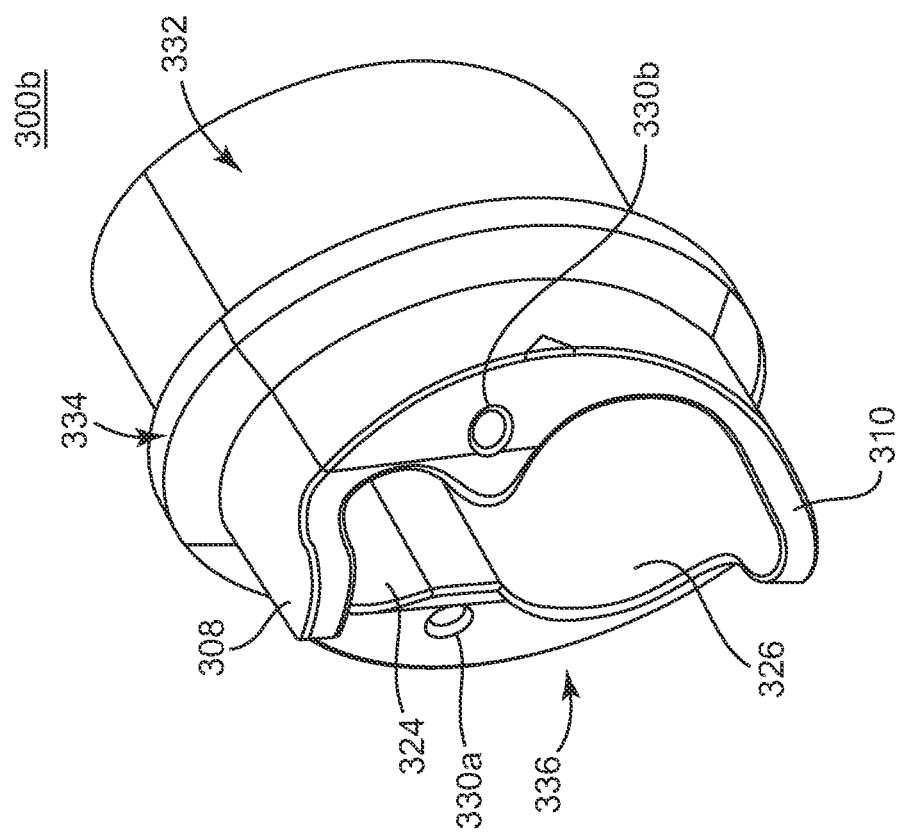
FIG. 13B is an enlarged, perspective view of an introducer proximal link of the instrument of FIG. 11.

The proximal link 300b is shown in greater detail in FIG. 13B and includes a base 332, an annular flange 334, and a link body 336. With additional reference to FIG. 11, the base 332 is tubular, configured for mounting to the proximal portion 286 of the introducer 254. The flange 334 extends radially relative to the base 332 and serves as an abutment surface upon assembly to the proximal portion 286. Finally, the link body 336 is akin to the intermediate link 300a (FIG. 13A) previously described, and thus includes the flanges 308, 310, the passages 324, 326, and the longitudinal bores 330a, 330b previously described.

Figure 14:
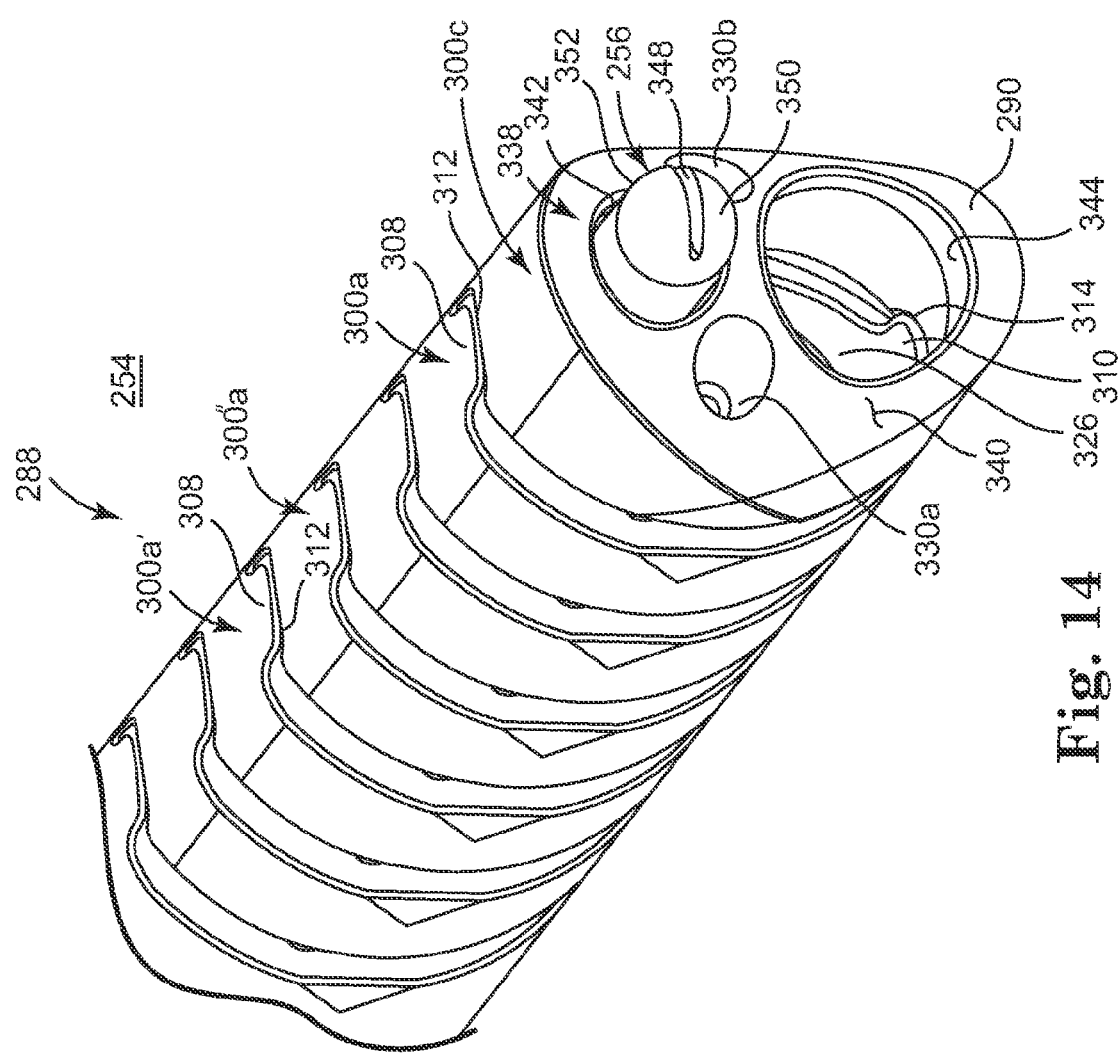
FIG. 14 is an enlarged, perspective view of the introducer of the instrument of FIG. 10.

The distal link 300c is shown in greater detail in FIG. 14. The distal link 300c includes a frame 338 forming the grooves 312, 314 and the longitudinal bores 330a, 330b as previously described. The frame 338 terminates at a closed face 340 that can otherwise serve as the distal end 290 of the introducer 254. The frame 338 further forms passage 342 sized to rotatably maintain the nozzle 256. The passage 342 is commensurate with the first passage 324 (hidden in the view of FIG. 14, but shown in FIG. 13A) of the intermediate links 300a, such that the nozzle 256 will be aligned with the irrigation duct carried thereby. Similarly, an aspiration inlet 344 is defined, commensurate with the second passage 326 (referenced generally in FIG. 14 and best shown in FIG. 13A) associated with the intermediate links 300a. Thus, the aspiration inlet 344 is fluidly connectable (or carries) the aspiration duct (e.g., the suction tubing 270 of FIG. 12B).

Upon final assembly, and with reference to FIGS. 11 and 14, the links 300 are assembled over the second irrigant delivery tube 298 (FIG. 12B) and the suction tubing 270 (FIG. 12B), with the proximal link 300b being assembled to a leading end 346 of the proximal portion 286. The intermediate links 300a are consecutively assembled distal the proximal link 300b. In this regard, an articulatable relationship is established therebetween. For example, relative to the first and second intermediate links 300a', 300a'' identified in FIG. 14, the first flange 308 of the first link 300a' rotatably nests within the first groove 312 of the second intermediate link 300a''. Although hidden in FIG. 14, a similar relationship is established between the second flange of the first intermediate link 300a' and the second groove of the second intermediate link 300a". The distal portion 288 terminates at the distal link 300c, that is otherwise rotatably associated with the flanges 308, 310 of the intermediate link 300a adjacent the distal link 300c via the grooves 312, 314.

As shown, the distal link 300c maintains the nozzle 256. The nozzle 256 can, in some embodiments, be identical to the nozzle 54 (FIG. 7) previously described, such that a detailed explanation is omitted. In general terms, and with specific reference to FIG. 14, the nozzle 256 is configured to generate a fan-like spray pattern, and is rotatably maintained by, or assembled to, the distal link 300c at the passage 342. The fan-like spray pattern is created via a V-cut 348 formed at a leading, hemispherical end 350 of the nozzle 256. In some embodiments, and as shown in FIG. 14, the V-cut 348 is formed to extend along a side 352 of the nozzle 256 so as to produce a side-looking spray pattern (and thus cover more area with rotation of the nozzle 256 as described below). Alternatively, the V-cut 348 can be centrally formed relative to an axis of the nozzle 256. Even further, a wide variety of other configurations for the nozzle 256 are also acceptable.

Returning to FIG. 11, the first actuator assembly 258 is configured to provide user-controlled movement or articulation of the introducer distal portion 288 relative to the handle 252, and includes, in some embodiments, an actuator 354 and the pull wires 294a, 294b (omitted from the view of FIG. 11, but shown, for example, in FIG. 12A). The first and second pull wires 294a, 294b are assembled to the actuator 354 and extend to the introducer 254 as described below. With this configuration, movement of the actuator 354 is translated onto the wires 294a, 294b that in turn effectuate movement of the introducer 254, and in particular the distal portion 288, relative to the handle 252.

In some embodiments, the actuator 354 includes a control wheel 356 and opposing shoulders 358 (one of which is shown in FIG. 11). The control wheel 356 is rotatably assembled to the handle 252, with a portion thereof projecting externally relative to the handle 252 as best shown in FIG. 10. With this configuration, then, the control wheel 356 is available for being acted upon by a user (not shown) otherwise grasping the handle 252, such as by the user's fingers and/or thumb. Regardless, the wheel 356 is rotatable about a center point 360, and can include features (not shown) that selectively lock the wheel relative to the handle 252 (e.g., the ball and groove mechanism described above with respect to the actuator assembly 56 of FIG. 3).

The shoulders 358 extend from the wheel 356 in a generally axial direction relative to the center point 360, and each define a slot 362 sized to receive a corresponding one of the pull wires 294a, 294b (omitted from the view of FIG. 11, but shown in FIG. 12A). In this regard, distal and proximal gaps 363a, 363b (referenced generally) are established between the shoulders 358, sized for passage of the first irrigant delivery tube 276. With this configuration, then, the first irrigant delivery tube 276 passes through the actuator 354, extending to the fitting 274 as described below. In addition, the gaps 363a, 363b establish sufficient spacing such that the first irrigant delivery tube 276 does not impede or obstruct rotation of the control wheel 356 about the center point 360. Regardless, and as alluded to above, the pull wires 294a, 294b extend from a corresponding one of the shoulders 358, and through the introducer 254. For example, the pull wires 294a, 294b extend through one of the longitudinal bores 330a, 330b (FIG. 12B) formed by the links 300. Regardless, the pull wires 294a, 294b extend to, and are attached at, the distal link 300c.

Figure 15:
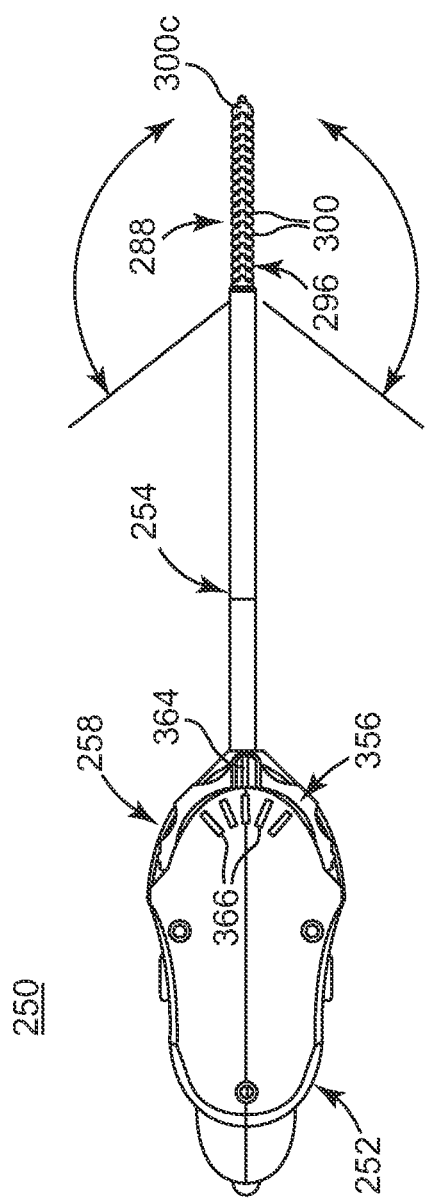
FIG. 15 a top view of the instrument of FIG. 10.

With reference to FIG. 15, operation of the first actuator assembly 258 includes a user-applied force being placed upon the control wheel 356. Rotation of the control wheel 356 imparts a pulling force onto one of the first or second pull wires 294a, 294b (FIG. 12B), and a corresponding pushing force onto the other of the wires 294a, 294b. The pushing/pulling forces, in turn, are translated onto the distal link 300c. The articulating or pivotable relationship of the links 300 otherwise comprising the articulatable framework 296 allows the distal portion 288 to flex or articulate in response to the pushing/pulling forces. As a result, the distal portion 288 will bend or flex as described above as shown by arrows in FIG. 15. To better assist a user in remotely evaluating an extent of articulation of the distal portion 288 (with the introducer 254 otherwise inserted within a bodily structure and thus hidden from the user's direct vision), the control wheel 356 can further include a pointer 364 and the handle 252 can include indicia 366. The indicia 366 provides an indication of angle or extent of articulation; with this configuration, then, the user can evaluate the extent to which the distal portion 288 has been bent or flexed via alignment with the pointer 364 with a corresponding one of the indicia 366. Alternatively, the first actuator assembly 258 can assume a wide variety of other forms.

Returning to FIG. 11, the second actuator assembly 260 provides control over a rotational orientation of the nozzle 256 and includes a control wheel 368 and the fitting 274. The control wheel 368 is rotatably maintained by the handle 252 such that at least a segment 370 (best shown in FIG. 10) thereof is exteriorly exposed (and thus accessible by a user of the instrument 250) at any rotational position (as shown in FIG. 10). Regardless, the control wheel 368 is affixed to the first irrigant delivery tube 276 that, as previously described, is optionally relatively rigid. Further, the fitting 274 is configured to rotatably receive the first irrigant delivery tube 276 in a manner providing a constant, fluid tight seal. With this configuration, then, rotation of the control wheel 368 is translated onto the first irrigant delivery tube 276. The fitting 274 permits the first irrigant delivery tube 276 to rotate with the wheel 368, while at all times maintaining a fluid connection with the irrigation tubing 268. As previously described, the first irrigant delivery tube 276 extends through the introducer 254, and in particular the proximal portion 286. Further, the first irrigant delivery tube 276 is mounted to the second irrigant delivery tube 298 (FIG. 12B). Thus, rotation of the first irrigant delivery tube 276 is transferred onto the second irrigant delivery tube 298, which in turn is attached to the nozzle 256. As such, rotation of the control wheel 368 is imparted onto the nozzle 256. Alternatively, the second actuator assembly 260 can assume a variety of other forms and, in some embodiments, can be eliminated.

Returning to FIG. 1A, regardless of an exact construction of the biofilm removal surgical instrument 22 (e.g., the instrument 48 of FIG. 2, the instrument 250 of FIG. 10, or other biofilm removal surgical instrument configuration envisioned by the pending disclosure), other components of the system 20 can assume a variety of forms. For example, the fluid source 24 can include a pump 380 connected to a reservoir 382. In some embodiments, the pump 380 is a peristaltic pump, such as those typically used in association with surgical and/or endoscopic procedures, the pump 380 serving to pressurize a flow of fluid from the reservoir 382 to the instrument 22 as described below. The reservoir 382 can include one or more IV bags, for example, filled with an irrigant, including the irrigating fluids described in U.S. patent application Ser. No. 11/431,495 entitled "Biofilm Extracellular Polysaccharide Solvating (EPS) System," filed May 10, 2006, an entirety of the contents of which are incorporated herein by reference. In some embodiments, the irrigant includes medicaments, including those adapted to interfere with bacterial biofilm regrowth, surfactants, gels, antimicrobials, steroids, growth hormones, chemicals for reducing biofilm adhesion force, and others.

The fluid source 24 is connected to the instrument 22, via the fluid connector 30, which is in some embodiments a tubing set. For example, the fluid connector 30 can be in fluid communication with (or formed as part of) the irrigation tubing 66 (FIG. 2), 268 (FIG. 11) such as by a port (not shown) that, in turn, is in fluid communication with the nozzle 44 as previously described. Further, the connector 32 can include an auxiliary inlet or port (not shown) for introducing medicaments into irrigant (not shown) flowing from the fluid source 24, for example, medicaments such as those previously referenced.

The vacuum source 26 (referenced generally) is adapted to provide an aspiratory or vacuum flow to the instrument 22 via the vacuum connector 32. The vacuum source 26 can include a collection canister 384 fluidly connecting a source of negative pressure (not shown) to the vacuum connector 32. The vacuum connector 32 is placed into fluid communication with, or is formed as part of, the suction tubing/aspiration duct 68 (FIG. 2), 270 (FIG. 11) and the source of negative pressure 26. The suction tubing/aspiration duct 68, 270, in turn, is in fluid communication with the aspiration inlet 184 (FIG. 7), 344 (FIG. 13C) formed or maintained by the introducer 42. In this manner, the aspiration inlet 184, 344 is in fluid communication with the vacuum source 26 such that an aspiratory flow can be "pulled" through the suction tubing/aspiration duct 68, 270. Additionally, in some embodiments, the canister 384 serves as a disposal means, such as a disposal tank, for collecting debris and other matter aspirated during use of the instrument 22, including those generally used in surgical and/or endoscopic procedures.

As previously referenced, the controller 28 controls operation of the system 20 and is designed as being physically associated with the fluid source 24, although the controller 28 is optionally a stand-alone device or physically associated with any of the other system components, including, for example, the connector 47 provided with the instrument 22. The controller 28 can assume a variety of forms capable of performing various functions and can include a microchip, a memory, and/or other appropriate controller electronics.

The controller 28 is placed in communication with the instrument 22 and the fluid source 24. For example, the controller 28 can be electronically connected to the trigger assembly 45 of the instrument 22 by the connector 47. The controller 28 can also be placed in direct or indirect communication with the fluid source 24 and/or the vacuum source 26 via wiring or alternative means as appropriate, for example using wireless transmitters and receivers. Regardless, in some embodiments, actuation of the trigger assembly 45 sends a signal to the controller 28 that, in turn, activates the fluid source 24 to provide a flow of irrigant to the instrument 22 as desired. In some embodiments, the controller 28 can further control operations of the vacuum source 26, either directly or indirectly. Along these lines, in other configurations, the controller 28 can be programmed or adapted to operate the system 20 according to a variety of desired irrigation and/or aspiration profiles, including ramp actuation, time delays, varied flow patterns, and others. For example, in some embodiments, the system 20 can further include a foot switch 386 or similar device electronically connected to the controller 28, with the foot switch 386 being operated by a user (not shown) to control operation of the instrument 22, the fluid source 24, and/or the vacuum source 26. In other embodiments, the foot switch 386 can be directly connected to the vacuum source 26 for controlling operation thereof.

As referenced above, some embodiments of the surgical biofilm removal system in accordance with the present disclosure further include the endoscope 34 as reflected by the system 20' of FIG. 1B. The endoscope 34 can be of a type known in the art and generally includes various optical components adapted to image internal bodily structures. In general terms, the endoscope 34 includes a handle 388 and an insertion portion 390 that defines a working end 392. The insertion portion 390 is adapted to be disposed inside a human body, with the working end 392 positioned at a target site to be imaged. "Imaging," "adapted to image," and similar language should be understood to be inclusive of direct visualization through the optical components of the endoscope 34 as well as electronic visualization and/or data analysis via electronic imaging, for example using the imaging device 38 or other electronics.

With many endoscope configurations, the light source 36 is provided to the endoscope 34 that in turn directs the emitted light to the working end 392 in illuminating an internal bodily structure or other target site being imaged, with associated images, or image data, being transmitted back from the working end 392 and to the imaging device 38 via the endoscope 34.

With the above in mind, the imaging device 38 is optionally an image sensor, such as a video camera, display, and/or other imaging electronics, including those typically used in association with endoscopic procedures. The imaging device 38 can be a standalone component, or can be linked to the controller 28. Regardless, and as is conventional known, the imaging device 38 and the endoscope 34 are used for imaging before, during, and/or after a surgical procedure using the instrument 22.

Figure 16:
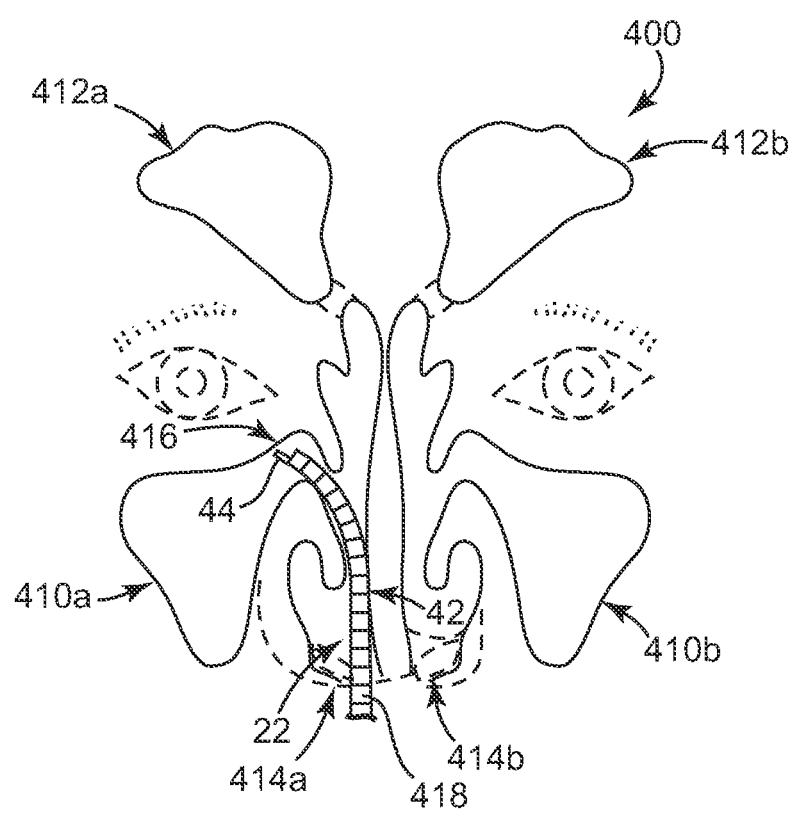
FIG. 16 illustrates methods of removing bacteria biofilm relative to a human anatomy in accordance with principles of the present disclosure.

Regardless of whether the endoscope 34 and related components 36, 38 are provided with the system 20, 20', the surgical biofilm removal system 20, 20' can be employed to perform a variety of procedures at various anatomical locations of the patient. By way of but one example, FIG. 16 illustrates internal bodily structures 400 of a patient, including sinus cavities such as the maxillary sinuses 410a, 410b and front sinuses 412a, 412b, which are accessed through nares 414a, 414b. It should be noted that external features of the patient, including the nares 414a, 414b, are shown in dashed lines. For some procedures in which the system 20, 20' is useful (e.g., a patient suffering from chronic rhinosinusitis), a first target site 416 can be designated in association with a surface of the maxillary sinus 410a for description of a surgical methodology for substantially removing a layer of biofilm. It should be understood, however, that similar principles apply across embodiments, including a variety of target sites associated with a variety of internal bodily structures, such as sinus cavities (e.g., the maxillary, frontal, sphenoid, etc.), cavities of the ear (the middle ear and others), etc. With this in mind, in some embodiments, the first target site 416 is ciliated epithelium of the maxillary sinus 410a that has an associated layer of bacteria and associated biofilm (not shown). In other embodiments, the target site 416 is an artificial structure (not shown), such as sinus packing or a stent covered with a layer of bacterial biofilm, for example.

With combined reference to FIGS. 1A and 16, and with the foregoing description of the system 20 in mind, some methods of removing bacterial biofilm (not shown) from the target site 416 (or any other target site internal to the patient) include: arranging the system 20; inserting the introducer 42 of the instrument 22 into the maxillary sinus 410a; aiming the nozzle 44) at the target site 416; delivering a pressurized flow of irrigant (not shown) from the nozzle 44 to the target site 416 to disrupt and remove a substantial amount of the bacterial biofilm; and aspirating the irrigant, removed biofilm, and/or bodily secretions (not shown) away from the target site 416 via the aspiration inlet 184 (FIG. 7), 344 (FIG. 14). Either of the instruments 48 (FIG. 2) or 250 (FIG. 10) can be employed in the methodologies described below (as can other configurations envisioned by the present disclosure), such that reference is made to the general instrument configuration 22 of FIGS. 1A and 1B.

In some embodiments, and with additional reference to FIG. 1B, the endoscope 34 and related components 36, 38 are provided and are employed in properly positioning the introducer 42/nozzle 44 relative to the target site 416. Along these same lines, a functional endoscopic sinus surgery (FESS) is also performed prior to, or concurrently with, insertion of the introducer 42. For example, the endoscope 34 and/or the instrument 22 is optionally adapted for, and/or used in combination with other implements as desired for, gaining access to the target site 416 as part of an FESS procedure.

Arranging the system 20 or 20' according to some embodiments includes connecting the endoscope 34 to the light source 36 and the imaging device 38. Similarly, the instrument 22 is connected to the fluid source 24 and the vacuum source 26 as appropriate. In this regard, connection between the instrument 22 and the fluid source 24 can be achieved via the controller 28. Regardless, the instrument 22 is electronically connected to the controller 28. Additionally, a sterile barrier 420 (illustrated schematically in FIGS. 1A and 1B), such as sheeting or others commonly used in surgical and/or endoscopic procedures, is positioned around the instrument and the patient is some embodiments to help maintain a sterile operating environment.

As referenced above, although some embodiments of acting upon a target site to remove a layer of biofilm are described with reference to the maxillary sinus 410a and the target site 416, it will be understood that biofilm removal at other target sites and/or other cavities, including sinus cavities or cavities of the middle ear (not shown) can proceed in a substantially similar manner. With this in mind, the endoscope 34 is initially optionally used to image the target site 416 or other internal bodily structures prior to, during, and/or following operation of the instrument 22. Though only the instrument 22 (and in particular the introducer 42) is shown in FIG. 16 as being inserted into the maxillary sinus 410a, it will be understood that both the endoscope 34 and the introducer 42 can be concurrently disposed in the maxillary sinus 410a (or other bodily cavity) in some embodiments.

Regardless, inserting the introducer 42 into the maxillary sinus 410a includes a practitioner (not shown) grasping the handle 40 (FIG. 1A) and inserting a distal portion 418 into the naris 414a, and toward the maxillary sinus 410a. In this regard, where provided, the endoscope 34 is similarly inserted and acquires images (via the imaging device 38) prior to, during, or after insertion of the introducer 42 in order to assist the practitioner in guiding and/or aiming the nozzle 44 at the target site 416.

With additional reference to FIGS. 9 and 15, the distal portion 418 is then selectively bent or articulated by the user (e.g., via the first actuator assembly 56 of FIG. 9 or the first actuator assembly 258 of FIG. 15) to "aim" the nozzle 44 in a desired direction and/or to facilitate insertion of the introducer 42 into the maxillary sinus 410a. As the nozzle 44 approaches the target site 416, the distal portion 418 is further articulated to address an angle of attack defined by the nozzle 44 relative to the target site 416. In this regard, the practitioner can evaluate whether the nozzle 44 is properly "aimed" or otherwise disposed relative to the target site 416 via the endoscope 34 and the imaging device 38. In some embodiments, the practitioner can identify the target site 416 by observing the presence/location of the layer of biofilm, for example by evaluating images displayed to the user via the imaging device 38.

Once positioned as desired, the user (not shown) then prompts delivery of a pressurized flow of irrigant to the target site 416 to effectuate removal or eradication of a substantial amount of the bacterial biofilm (not shown) from the target site by squeezing the actuator 46. In response to this actuation, a signal is sent to the controller 28 that in turn prompts activation of the fluid source 24 to provide the flow of irrigant through the irrigation duct described above and thus the nozzle 44. It is contemplated that the flow of irrigant will be directed through the nozzle 44 at a variety of flow rates according to various embodiments, including a flow rate from about 2 mL/sec to about 12 mL/sec. In some embodiments, the system 20, 20' is adapted to cause pulse flow through the nozzle 44, and other substantially continuous flow, and in still others, a flow pattern other than pulsed or substantially continuous flow.

The flow of irrigant dispensed from the nozzle 44 directly impinges upon, or otherwise directly strikes, the target site 416 to mechanically agitate or disrupt and remove a substantial portion, or substantially all, of the biofilm (not shown). In other words, the nozzle 44 is able to be aimed directly at the target site 416 as previously described when sufficiently accessed with the introducer 52, 254, such that a mechanical "scrubbing" action is accomplished. It should be noted that the pressure and/or flow rate of the irrigant is selected to promote mechanical removal of the biofilm without substantial damage to underlying tissue, such as a ciliated epithelium layer. For example, a pressure of less than about 50 psi can be selected, although other pressures are also acceptable.

With continued flow of the pressurized irrigant from the nozzle 44, the user optionally periodically and/or continuously rotates the nozzle 44 via an actuator assembly (e.g., the second actuator assembly 58 of FIG. 2 or the second actuator assembly 260 of FIG. 11). As previously described, in some embodiments, the nozzle 44 generates a line, fan spray pattern; with rotation of the nozzle 44, then, a path is effectively "swept" at or across the target site 416, such that the introducer 42 can remain relatively stationary while treating a relatively large area. With this approach, the ability to accurately locate the nozzle 44 relative to the target site 416 is of less concern in that a relatively large surface area can be acted upon by the pressurized irrigant delivered from the nozzle 44. In fact, in some embodiments, the relatively large treatment area reduces the need for an endoscope having complicated optics, and can in fact eliminate the need for use of a dedicated endoscope with the instrument 22. Alternatively, however, the nozzle 44 can assume a wide variety of other configurations and/or the ability to rotate the nozzle 44 relative to the introducer 42 need not be provided.

In some embodiments, aspiration of bacterial biofilm, bacteria, mucous, secretions, dead tissue, or other unwanted matter is accomplished using the aspiration inlet 184 (FIG. 7), 344 (FIG. 14), for example during and/or after dispensing the irrigant (not shown) against the target site 416. The instrument 22, is operated to selectively or continuously activate the vacuum source 26 in response to the user operating the actuator 46 and/or the foot switch 386, for example concurrently with irrigation and/or with some time differential (for example, before or after irrigation). The unwanted matter is removed in proximate the target site 416 as optionally directed to the biological collection canister 384 otherwise associated with the vacuum source 32.

The systems and methods described above are highly useful in surgically treating various maladies associated with multiple different and anatomical locations or target sites. For example, in addition to sinus and inner ear target sites, the systems and methods of the present disclosure can be used to treat target site(s) in patients lungs (e.g., cystic fibrosis and the respiratory epithelium of the lungs), urological and/or gynecological (e.g., urinary tract infections), etc.

The system and methods of the present disclosure provide a marked improvement over previous techniques and devices used to treat various ailments, such as chronic rhinosinusitis. By effectuating biofilm eradication using a focused, pressurized fluid, a more complete treatment is provided to the patient on a minimally invasive basis. Further, with sinus and other applications, drainage pathway(s) are restored, ventilation of the treatment site is provided (thus minimizing opportunities for biofilm regrowth), and other functional and endoscopic sinus surgery treatments can be provided (e.g., topical application of medicaments, irrigation, etc.).

In view of the above, a method for eradicating bacterial biofilm from a target site within an internal bodily cavity using the instrument 22 (e.g., the instrument 48 of FIG. 2 or the instrument 250 of FIG. 10) is provided according to some embodiments. It should be noted that the various functions and advantages of the system 20, 20' are optionally provided according to other, related embodiments, such as those described below in association with FIGS. 17-22.

Figure 17:
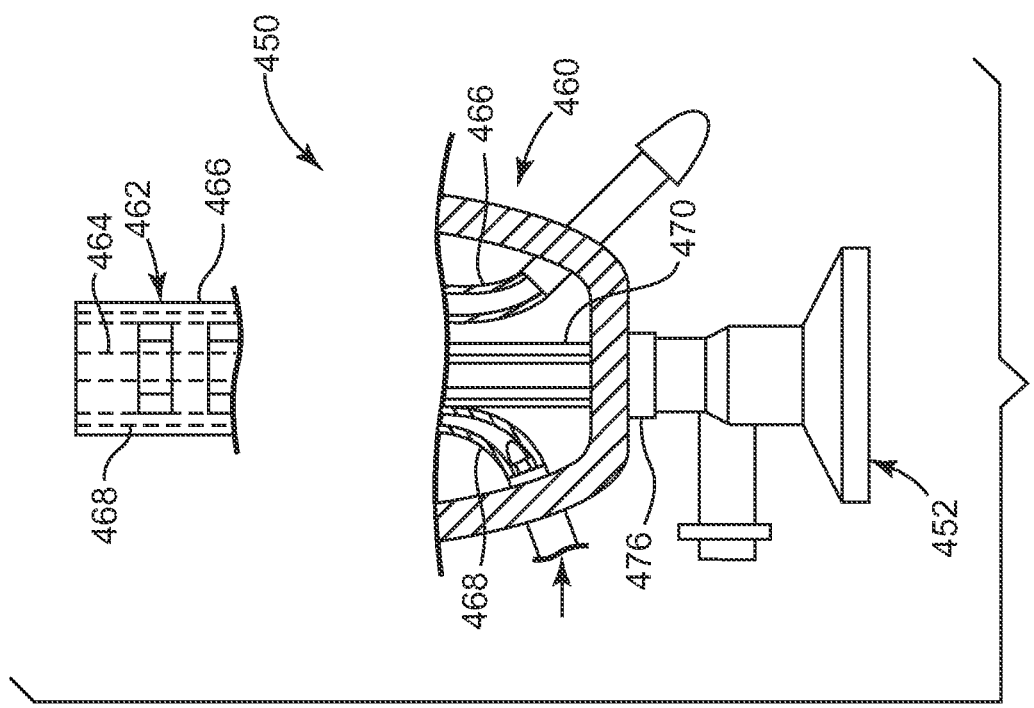

FIG. 17 shows a biofilm removal surgical instrument 450 according to some embodiments, where the instrument 450 includes features for receiving an endoscope 452. The instrument 450 is substantially similar to the instrument 22 (FIG. 1A) with corresponding components including a handle 460, an actuator assembly (not shown), an introducer 462 including a flexible, distal portion 464, an irrigation duct 466, and an aspiration duct 468. The instrument 450 further includes or defines an endoscope duct 470 extending through the introducer 462, with the handle 460 forming an endoscope port 476 for slidably receiving the endoscope 452. For reference, FIG. 17 shows a side view of the instrument 450 with a section of the handle 452 and the introducer 462 removed to assist in understanding.

Figure 18:
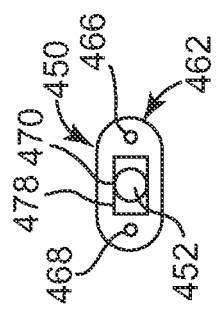
FIGS. 17 and 18 show a surgical biofilm removal instrument according to some other embodiments.

With reference between FIG. 17 and FIG. 18, the introducer 462 can be similar to the introducer 42 (FIG. 1A), and further defines an endoscope guide (not shown), which optionally includes an optical window 478 for protecting a working end (not shown) of the endoscope 452. The endoscope duct 470 is optionally a hollow tube, or cannula, extending between the endoscope port 476 and the endoscope guide. It should also be noted that according to some embodiments, the endoscope duct 468 is formed by the interior of the handle 460 and the introducer 462, or portions thereof.

In use, the endoscope 452 is inserted into the endoscope port 476 and slid through the endoscope duct 468 such that the working end (not shown) resides in the endoscope guide and abuts, or is proximate, the optical window 478 where appropriate. The endoscope 452 is optionally adapted to releasably mate with, or otherwise be releasably secured to, the endoscope port 476 and/or a portion of the handle 460.

As described above in association with some embodiments of the instrument 22, the instrument 450, and in particular the distal portion 464 of the introducer 462, is optionally adapted to be actuated, or selectively bent, through a plurality of angles of attack similar to the instrument 22, to direct irrigant and/or aspiratory flow to a desired target site. In some embodiments, the endoscope 452 is a flexible endoscope such that selective bending of the introducer 462 also allows the working end (not shown) of the endoscope 452 to be aimed at image target sites, such as the target site 416 (FIG. 16) prior to, during, or after undergoing a biofilm removal procedure.

Figures 19, 20:
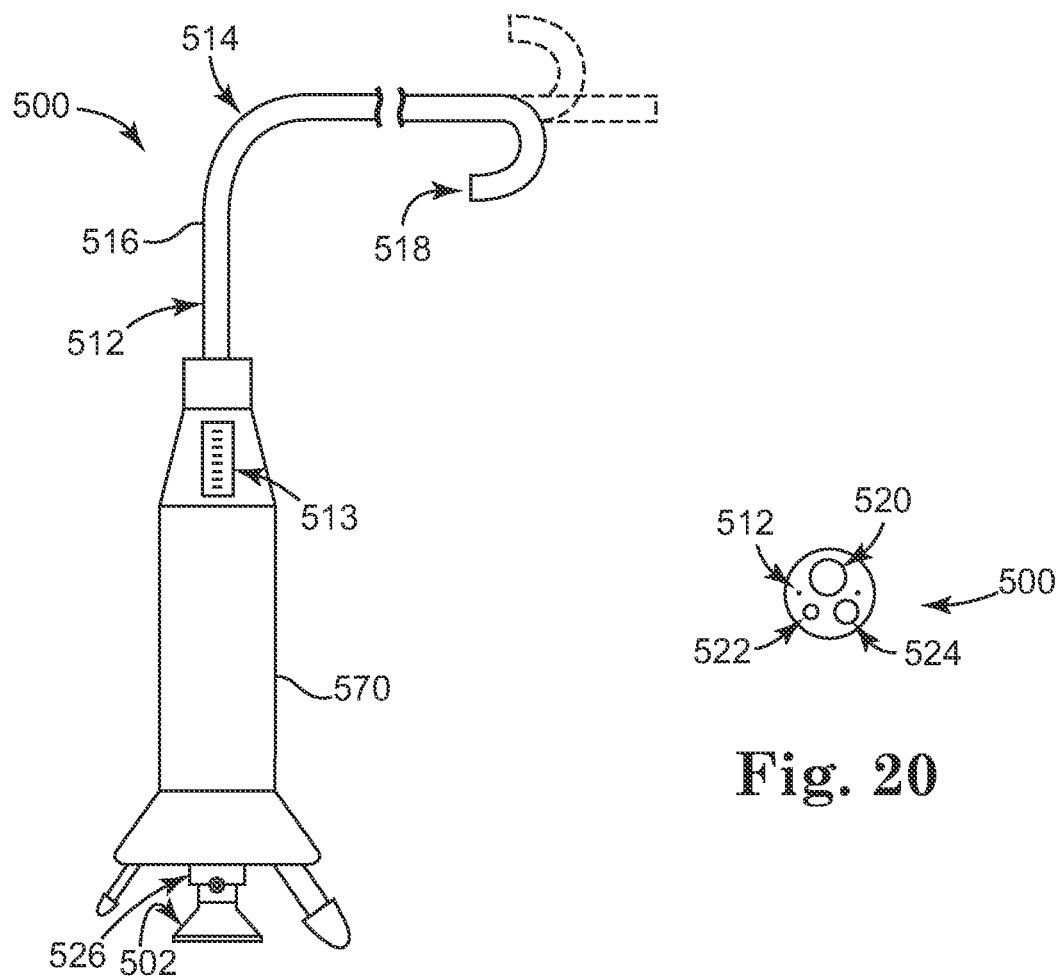
FIGS. 19 and 20 show a surgical biofilm removal instrument according to still other embodiments.

FIG. 19 shows another biofilm removal surgical instrument 500 according to some embodiments, where the instrument 500 includes features similar to those of the instrument 450 (FIGS. 17 and 18) for receiving an endoscope 502, and is further adapted to be flexibly inserted into a bodily cavity as a flexible catheter. In particular, the instrument 500 is substantially similar to the instrument 450 with corresponding components including a handle 510, an introducer 512, an actuator assembly 513 (referenced generally), an irrigation duct (not shown), an aspiration duct (not show), and an endoscope duct (not shown). The introducer 512 includes a distal portion 514 and a proximal portion 516. The proximal portion 516 and the distal portion 514 are sized and shaped and otherwise adapted be used as a flexible catheter, with the distal portion 514 is configured to be selectively articulatable, for example as previously described in association with other embodiments. The introducer 512 terminates at a distal end 518. As shown in FIG. 20, the distal end 518 optionally carries a nozzle 520 (illustrated generally) that is fluidly connected to the irrigation duct (not shown) otherwise extending through the introducer 512. In addition, FIG. 20 illustrates the aspiration duct 522.

With reference between FIG. 19 and FIG. 20, the introducer 512 is similar to the introducer 462 (FIG. 17), and further defines an endoscope guide (not shown), which optionally includes an optical window 524 (FIG. 20) for protecting a working end (not shown) of the endoscope 502. The endoscope duct (not shown) is optionally a hollow tube, or cannula, extending between an endoscope port 526 (FIG. 19) and the endoscope guide (not shown). It should also be noted that according to some embodiments, the endoscope duct is formed by the interior of the handle 510 and the introducer 512, or portions thereof.

In use, the endoscope 502 is inserted into the endoscope port 526 and slid through the endoscope duct (not shown) such that the working end (not shown) resides in the endoscope guide (not shown) and abuts, or is proximate, the optical window 524 where appropriate. The endoscope 502 is optionally adapted to releasably mate with, or otherwise be releasably secured to, the endoscope port 526 and/or a portion of the handle 510.

As described above, the instrument 500, and in particular the proximal portion 516 is substantially flexible and usable as a flexible catheter to gain access to internal bodily structures. In some embodiments, the distal portion 514 is adapted to be actuated, or selectively bent, through a plurality of angles of attack similar to the instrument 22 (FIG. 1A) to direct irrigant and/or aspiratory flow to a desired target site. In some embodiments, the endoscope 502 is a flexible endoscope such that selective bending of the instrument 500 also allows the working end (not shown) of the endoscope 502 to be aimed at image target sites, such as the target site 416 (FIG. 16) prior to, during, or after undergoing a biofilm removal procedure.

Figure 21:
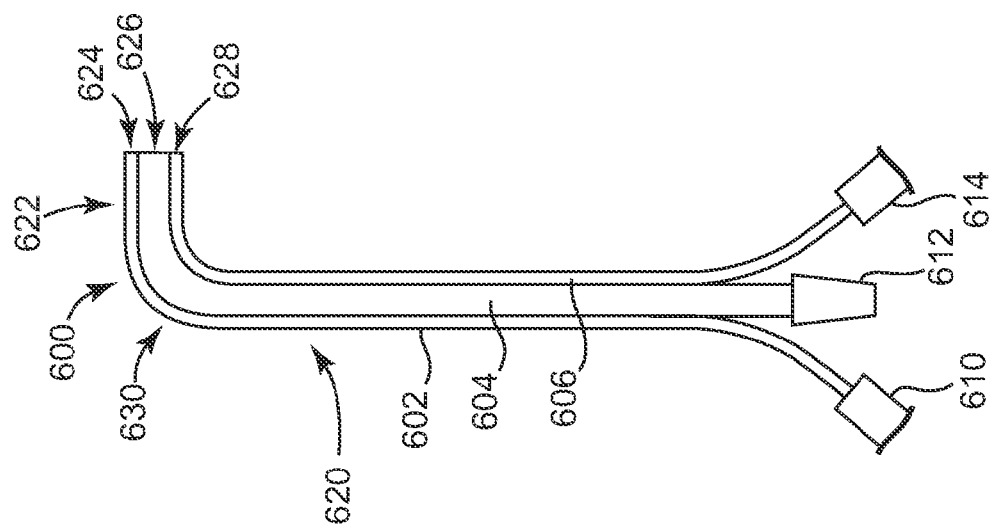

FIG. 21 shows another biofilm removal surgical instrument 600 for use with an endoscope (not shown) from a side view according to some embodiments, where the instrument 600 includes an irrigation duct 602, an aspiration duct 604, and an endoscope duct 606. Each of the ducts 602, 604, 606 is formed as an elongate, hollow, and tubular member. The ducts 602, 604, 606 form an irrigation port 610, an aspiration port 612, and a endoscope port 614, for connection to corresponding bacterial biofilm removal system components as described above in association with the system 20 (FIG. 1A). The ducts 602, 604, 606 are secured relative to one another and combine to define a proximal portion 620 and a distal portion 622 of the instrument 600. The irrigation duct 602 forms or maintains a nozzle 624. The aspiration duct 604 forms an inlet end 626 for aspirating matter from a target site 416 (FIG. 16). In turn, the endoscope duct 606 is adapted to receive the endoscope (not shown) and optionally includes an optical window 628 for protecting the endoscope during use.

Figure 22:
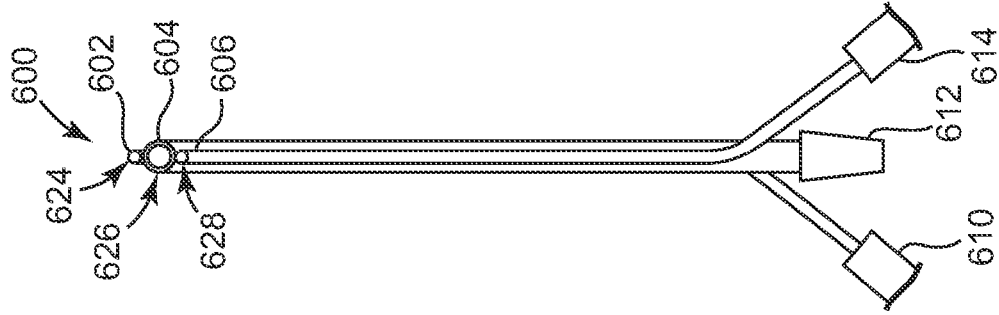
FIGS. 21 and 22 show a surgical biofilm removal instrument according to yet other embodiments.

With reference between FIG. 21 and FIG. 22, the distal portion 622 defines a bend 630 relative to the proximal portion that is independently maintained by the instrument 600. In some embodiments, one or more of the ducts 602, 604, 606, or portions thereof, are substantially rigid such that the bend 630 is independently maintained. In some embodiments, one or more of the ducts 602, 602, 604, 606, are substantially malleable such that the bend 630, or additional bends (not shown) can be defined and independently maintained by the instrument 600.

In use, the endoscope (not shown) is inserted into the endoscope port 614 and slid through the endoscope duct 606 such that the working end (not shown) of the endoscope abuts, or is proximate, the optical window 628. The endoscope 602 is optionally adapted to releasably mate with, or otherwise be releasably secured to, the endoscope port 614. In some embodiments, the endoscope 602 is a flexible endoscope such that the bend 630, including a rigid bend or bends, or malleable bend(s) of the instrument 600 result in a corresponding bend in an insertion tube (not shown) of the endoscope to aim and maintain an angle of attack of the working end of the endoscope, the nozzle 624, and the distal inlet 626 relative to a desired target site.

Although the present invention has been described with reference to preferred embodiments, workers skilled in the art will recognize that changes can be made in form and detail without departing from the spirit and scope of the present invention. For example, the duct assemblies described herein are optional components for the biofilm removal system, and thus can be eliminated, as can one or more of the other components apart from the surgical instrument.

What is claimed is:

1. A system for removal of bacterial biofilm from a target site of a human patient, the system comprising:
   a surgical instrument for removing bacterial biofilm from the target site, the instrument comprising:
      an elongate introducer adapted for minimally invasive surgical insertion into a human patient, the introducer including a proximal portion and a distal portion terminating at a distal end, the distal portion being transitionable between a plurality of bend angles relative to the proximal portion, wherein the instrument is adapted to independently maintain the distal portion at each of the plurality of bend angles relative to the proximal portion;
      an irrigation duct for conveying irrigant;
      a nozzle rotatably mounted to the introducer and in fluid communication with the irrigation duct, the nozzle being maintained relative to the distal end of the introducer and being adapted to dispense pressurized fluid from the irrigation duct toward a layer of bacterial biofilm to disrupt the bacterial biofilm from the target site;
      a first actuator assembly adapted to selectively rotate the nozzle relative to the introducer;
      wherein the instrument further includes a handle maintaining the introducer, and further wherein the first actuator assembly includes:
         a first wheel rotatably secured to the handle;
         a rigid irrigation duct segment connected to and extending from the wheel; and
         a flexible irrigation duct segment extending between the rigid irrigation duct segment and the nozzle.

2. The system of claim 1, further comprising:
   an endoscope system including an endoscope and an imaging device.

3. The system of claim 1, further comprising:
   a vacuum source; and
   an aspiration duct in fluid communication with the vacuum source, the aspiration duct extending through the introducer and terminating at an aspiration inlet for aspirating matter from the target site.

4. The system of claim 1, wherein the proximal portion of the introducer is substantially rigid, the distal portion of the introducer is substantially flexible, and the instrument further comprises:
   a second actuator assembly adapted to transition the distal portion of the introducer between the plurality of bend angles.

5. The system of claim 4, wherein:
   the second actuator assembly comprises:
      a first wire and a second wire each secured to the distal portion of the introducer;
      a second wheel rotatably secured relative to the handle;
      wherein the distal portion defines a first side and a second side opposite the first side; and
      further wherein, the first wire mechanically connects the second wheel and the first side of the distal portion, and the second wire mechanically connects the second wheel and the second side of the distal portion.

6. The system of claim 5, wherein the distal portion includes a plurality of pivotably connected links.

7. The system of claim 6, wherein each link includes a frame and opposing flanges.

8. The system of claim 1, wherein at least a portion of the introducer is substantially articulatable such that the distal portion is adapted to be transitioned between, and independently maintained at, the plurality of bend angles relative to the proximal portion.

9. The system of claim 1, wherein the nozzle is configured to generate a fan-type spray pattern.

10. The system of claim 1, wherein the introducer terminates at a distal face, and further wherein the nozzle projects from the distal face and is arranged to direct irrigant from the irrigation duct in a direction away from the distal face.

11. A method of disrupting bacterial biofilm from a target site of a human patient, the method comprising:
    providing a bacterial biofilm removal system including:
       a surgical instrument for removing the bacterial biofilm from the target site having an elongate introducer adapted for minimally invasive surgical insertion into the human patient including a proximal portion and a distal portion terminating at a distal end, the distal portion being articulatable and transitionable between a plurality of bend angles relative to the proximal portion, wherein the instrument is adapted to independently maintain the distal portion at each of the plurality of bend angles relative to the proximal portion, wherein the introducer maintains an irrigation duct for conveying irrigant and a nozzle in fluid communication with the irrigation duct, wherein the nozzle is positioned at the distal end and is rotatably mounted to the introducer and adapted to dispense pressurized fluid from the irrigation duct toward a layer of bacterial biofilm to disrupt the bacterial biofilm from the target site;

the surgical instrument further comprising a first actuator assembly adapted to selectively rotate the nozzle relative to the introducer; and wherein the instrument further includes a handle maintaining the introducer, and further wherein the first actuator assembly includes:
- a first wheel rotatably secured to the handle;
- a rigid irrigation duct segment connected to and extending from the first wheel; and
- a flexible irrigation duct segment extending between the rigid irrigation duct segment and the nozzle;

surgically inserting the distal portion of the introducer into the patient;

delivering the nozzle proximate the target site, the target site including a layer of bacterial biofilm adhered to a surface;

rotating the nozzle relative to the introducer following delivering of the nozzle proximate the target site; and dispensing a pressurized flow of irrigant through the nozzle toward the target site to mechanically remove a substantial portion of the layer of bacterial biofilm from the surface.

12. The method of claim 11, the method further comprising: spatially articulating the distal end relative to the handle of the instrument to adjust an angle of attack of the nozzle.

13. The method of claim 12, wherein spatially articulating the distal end includes:
- delivering the nozzle to a first location relative to the target site to define a first angle of attack of the nozzle relative to the target site;
- evaluating an effectiveness of the first angle of attack;
- actuating a second actuator external the patient to effectuate a bend in the distal portion to adjust the angle of the nozzle from the first angle of attack to a second angle of attack.

14. The method of claim 11, wherein the fluid is dispensed from the nozzle while rotating the nozzle.

15. The method of claim 11, wherein the instrument has an aspiration duct extending through the introducer and terminating at an aspiration inlet adjacent the nozzle, the method further comprising:
- aspirating the removed bacterial biofilm and the dispensed irrigant through the aspiration inlet.

16. The method of claim 11, wherein substantially all of the layer of bacterial biofilm is removed from the target site with the dispensed irrigant.

17. The method of claim 11, further comprising:
- delivering the working end of an endoscope proximate the target site;
- imaging the target site with the endoscope; and
- positioning the nozzle relative to the target site based upon the imaging.

18. The method of claim 11, further comprising applying a medicament to the target site through the irrigation duct, the medicament adapted to interfere with bacterial biofilm regrowth.

19. The method of claim 18, wherein the medicament is selected from the group consisting of: a surfactant, a gel, an antimicrobial, a steroid, a growth hormone, and combinations thereof.

20. The method of claim 11, wherein the flow of irrigant is directed through the nozzle at a flow rate from about 2 ml/s to about 12 ml/s.

21. The method of claim 11, wherein the target site is within a sinus cavity.

22. The method of claim 11, wherein the target site includes ciliated epithelium.

23. The method of claim 11, wherein the method is performed in treating chronic rhinosinusitis.

* * * * *